(12) United States Patent
Shreim et al.

(10) Patent No.: US 10,993,662 B2
(45) Date of Patent: *May 4, 2021

(54) NOSE SENSOR

(71) Applicant: MASIMO CORPORATION, Irvine, CA (US)

(72) Inventors: Samir Shreim, Irvine, CA (US); Vikrant Sharma, Santa Ana, CA (US); Philip Perea, Irvine, CA (US); Jennifer Rines, Carlsbad, CA (US); Clinton Robins, Lake Forest, CA (US); Chad Eichele, Lake Forest, CA (US); Yassir Kamel Abdul-Hafiz, Irvine, CA (US)

(73) Assignee: MASIMO CORPORATION, Irvine, CA (US)

( * ) Notice: Subject to any disclaimer, the term of this patent is extended or adjusted under 35 U.S.C. 154(b) by 440 days.

This patent is subject to a terminal disclaimer.

(21) Appl. No.: 15/913,691

(22) Filed: Mar. 6, 2018

(65) Prior Publication Data
US 2018/0192953 A1 Jul. 12, 2018

Related U.S. Application Data

(63) Continuation-in-part of application No. 15/451,288, filed on Mar. 6, 2017, now Pat. No. 10,537,285.
(Continued)

(51) Int. Cl.
*A61B 5/1455* (2006.01)
*A61B 5/00* (2006.01)
(Continued)

(52) U.S. Cl.
CPC .......... *A61B 5/6819* (2013.01); *A61B 5/0205* (2013.01); *A61B 5/02427* (2013.01);
(Continued)

(58) Field of Classification Search
CPC .............. A61B 5/1455; A61B 5/14551; A61B 5/14552; A61B 5/6819; A61B 5/0205;
(Continued)

(56) References Cited

U.S. PATENT DOCUMENTS

| 4,543,146 A | 9/1985 | Petcen |
| 4,685,464 A | 8/1987 | Goldberger et al. |

(Continued)

FOREIGN PATENT DOCUMENTS

| WO | WO 1993/005710 | 4/1993 |
| WO | WO 1996/013208 | 5/1996 |

(Continued)

OTHER PUBLICATIONS

International Preliminary Report on Patentability and Written Opinion received in PCT Application No. PCT/US2018/027833, dated Oct. 31, 2019.
(Continued)

*Primary Examiner* — Chu Chuan Liu
(74) *Attorney, Agent, or Firm* — Knobbe, Martens, Olson & Bear, LLP

(57) ABSTRACT

A patient monitor can noninvasively measure a physiological parameter using sensor data from a nose sensor configured to be secured to a nose of the patient. The nose sensor can include an emitter and a detector. The detector is configured to generate a signal when detecting light attenuated by the nose tissue of the patient. An output measurement of the physiological parameter can be determined based on the signals generated by the detector. The nose sensor can include a diffuser configured to disseminate light exiting from the emitter into or around a portion of the patient's body. The nose sensor can also include a lens configured to focus light into the detector.

17 Claims, 23 Drawing Sheets

Related U.S. Application Data which is a continuation-in-part of application No. 15/448,971, filed on Mar. 3, 2017, now abandoned.

(60) Provisional application No. 62/303,743, filed on Mar. 4, 2016.

(51) Int. Cl.
*A61B 5/024* (2006.01)
*A61B 5/145* (2006.01)
*A61B 5/08* (2006.01)
*A61B 5/0205* (2006.01)

(52) U.S. Cl.
CPC ........ *A61B 5/0816* (2013.01); *A61B 5/14532* (2013.01); *A61B 5/14546* (2013.01); *A61B 5/14551* (2013.01); *A61B 5/746* (2013.01); *A61B 5/7445* (2013.01); *A61B 2562/0242* (2013.01)

(58) Field of Classification Search
CPC ............ A61B 5/14532; A61B 5/14546; A61B 5/6826; A61B 5/02427; A61B 5/0059; A61B 5/6838; A61B 5/746; A61B 5/0816; A61B 5/7445
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,190,048 A | 3/1993 | Wilkinson |
| 5,247,931 A | 9/1993 | Norwood |
| 5,319,355 A | 6/1994 | Russek |
| 5,335,659 A | 8/1994 | Pologe |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| 5,383,469 A | 1/1995 | Vreman et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,724 A | 9/1998 | Gronvall |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,621 A | 9/2000 | Chin |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |

(56) References Cited

U.S. PATENT DOCUMENTS

| | | |
|---|---|---|
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,535,714 B2 | 3/2003 | Melker et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,909,912 B2 | 6/2005 | Melker |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,127,278 B2 | 10/2006 | Melker et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,313,425 B2 | 12/2007 | Finarov et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |

(56) References Cited

U.S. PATENT DOCUMENTS

| | | | |
|---|---|---|---|
| 7,509,154 | B2 | 3/2009 | Diab et al. |
| 7,509,494 | B2 | 3/2009 | Al-Ali |
| 7,510,849 | B2 | 3/2009 | Schurman et al. |
| 7,514,725 | B2 | 4/2009 | Wojtczuk et al. |
| 7,519,406 | B2 | 4/2009 | Blank et al. |
| 7,526,328 | B2 | 4/2009 | Diab et al. |
| D592,507 | S | 5/2009 | Wachman et al. |
| 7,530,942 | B1 | 5/2009 | Diab |
| 7,530,949 | B2 | 5/2009 | Al Ali et al. |
| 7,530,955 | B2 | 5/2009 | Diab et al. |
| 7,563,110 | B2 | 7/2009 | Al-Ali et al. |
| 7,593,230 | B2 | 9/2009 | Abul-Haj et al. |
| 7,596,398 | B2 | 9/2009 | Al-Ali et al. |
| 7,606,608 | B2 | 10/2009 | Blank et al. |
| 7,618,375 | B2 | 11/2009 | Flaherty |
| 7,620,674 | B2 | 11/2009 | Ruchti et al. |
| D606,659 | S | 12/2009 | Kiani et al. |
| 7,629,039 | B2 | 12/2009 | Eckerbom et al. |
| 7,640,140 | B2 | 12/2009 | Ruchti et al. |
| 7,647,083 | B2 | 1/2010 | Al-Ali et al. |
| D609,193 | S | 2/2010 | Al-Ali et al. |
| D614,305 | S | 4/2010 | Al-Ali et al. |
| 7,697,966 | B2 | 4/2010 | Monfre et al. |
| 7,698,105 | B2 | 4/2010 | Ruchti et al. |
| RE41,317 | E | 5/2010 | Parker |
| RE41,333 | E | 5/2010 | Blank et al. |
| 7,729,733 | B2 | 6/2010 | Al-Ali et al. |
| 7,734,320 | B2 | 6/2010 | Al-Ali |
| 7,761,127 | B2 | 7/2010 | Al-Ali et al. |
| 7,761,128 | B2 | 7/2010 | Al-Ali et al. |
| 7,764,982 | B2 | 7/2010 | Dalke et al. |
| D621,516 | S | 8/2010 | Kiani et al. |
| 7,785,262 | B2 | 8/2010 | Melker et al. |
| 7,791,155 | B2 | 9/2010 | Diab |
| 7,801,581 | B2 | 9/2010 | Diab |
| 7,820,108 | B2 | 10/2010 | Lampotang et al. |
| 7,822,452 | B2 | 10/2010 | Schurman et al. |
| RE41,912 | E | 11/2010 | Parker |
| 7,844,313 | B2 | 11/2010 | Kiani et al. |
| 7,844,314 | B2 | 11/2010 | Al-Ali |
| 7,844,315 | B2 | 11/2010 | Al-Ali |
| 7,865,222 | B2 | 1/2011 | Weber et al. |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,887,502 | B2 | 2/2011 | Ross et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,899,518 | B2 | 3/2011 | Trepagnier et al. |
| 7,904,132 | B2 | 3/2011 | Weber et al. |
| 7,909,772 | B2 | 3/2011 | Popov et al. |
| 7,910,875 | B2 | 3/2011 | Al-Ali |
| 7,914,460 | B2 | 3/2011 | Melker et al. |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,937,130 | B2 | 5/2011 | Diab et al. |
| 7,941,199 | B2 | 5/2011 | Kiani |
| 7,951,086 | B2 | 5/2011 | Flaherty et al. |
| 7,957,780 | B2 | 6/2011 | Lamego et al. |
| 7,962,188 | B2 | 6/2011 | Kiani et al. |
| 7,962,190 | B1 | 6/2011 | Diab et al. |
| 7,976,472 | B2 | 7/2011 | Kiani |
| 7,988,637 | B2 | 8/2011 | Diab |
| 7,990,382 | B2 | 8/2011 | Kiani |
| 7,991,446 | B2 | 8/2011 | Ali et al. |
| 8,000,761 | B2 | 8/2011 | Al-Ali |
| 8,008,088 | B2 | 8/2011 | Bellott et al. |
| RE42,753 | E | 9/2011 | Kiani-Azarbayjany et al. |
| 8,019,400 | B2 | 9/2011 | Diab et al. |
| 8,028,701 | B2 | 10/2011 | Al-Ali et al. |
| 8,029,765 | B2 | 10/2011 | Bellott et al. |
| 8,036,727 | B2 | 10/2011 | Schurman et al. |
| 8,036,728 | B2 | 10/2011 | Diab et al. |
| 8,046,040 | B2 | 10/2011 | Ali et al. |
| 8,046,041 | B2 | 10/2011 | Diab et al. |
| 8,046,042 | B2 | 10/2011 | Diab et al. |
| 8,048,040 | B2 | 11/2011 | Kiani |
| 8,050,728 | B2 | 11/2011 | Al-Ali et al. |
| 8,073,518 | B2 | 12/2011 | Chin |
| RE43,169 | E | 2/2012 | Parker |
| 8,118,620 | B2 | 2/2012 | Al-Ali et al. |
| 8,126,528 | B2 | 2/2012 | Diab et al. |
| 8,128,572 | B2 | 3/2012 | Diab et al. |
| 8,130,105 | B2 | 3/2012 | Al-Ali et al. |
| 8,145,287 | B2 | 3/2012 | Diab et al. |
| 8,150,487 | B2 | 4/2012 | Diab et al. |
| 8,175,672 | B2 | 5/2012 | Parker |
| 8,180,420 | B2 | 5/2012 | Diab et al. |
| 8,182,443 | B1 | 5/2012 | Kiani |
| 8,185,180 | B2 | 5/2012 | Diab et al. |
| 8,190,223 | B2 | 5/2012 | Al-Ali et al. |
| 8,190,227 | B2 | 5/2012 | Diab et al. |
| 8,203,438 | B2 | 6/2012 | Kiani et al. |
| 8,203,704 | B2 | 6/2012 | Merritt et al. |
| 8,204,566 | B2 | 6/2012 | Schurman et al. |
| 8,211,035 | B2 | 7/2012 | Melker et al. |
| 8,219,172 | B2 | 7/2012 | Schurman et al. |
| 8,224,411 | B2 | 7/2012 | Al-Ali et al. |
| 8,228,181 | B2 | 7/2012 | Al-Ali |
| 8,229,532 | B2 | 7/2012 | Davis |
| 8,229,533 | B2 | 7/2012 | Diab et al. |
| 8,233,955 | B2 | 7/2012 | Al-Ali et al. |
| 8,244,325 | B2 | 8/2012 | Al-Ali et al. |
| 8,255,026 | B1 | 8/2012 | Al-Ali |
| 8,255,027 | B2 | 8/2012 | Al-Ali et al. |
| 8,255,028 | B2 | 8/2012 | Al-Ali et al. |
| 8,260,577 | B2 | 9/2012 | Weber et al. |
| 8,265,723 | B1 | 9/2012 | McHale et al. |
| 8,274,360 | B2 | 9/2012 | Sampath et al. |
| 8,279,063 | B2 | 10/2012 | Wohltjen |
| 8,280,473 | B2 | 10/2012 | Al-Ali |
| 8,281,787 | B2 | 10/2012 | Burton |
| 8,301,217 | B2 | 10/2012 | Al-Ali et al. |
| 8,306,596 | B2 | 11/2012 | Schurman et al. |
| 8,310,336 | B2 | 11/2012 | Muhsin et al. |
| 8,315,683 | B2 | 11/2012 | Al-Ali et al. |
| RE43,860 | E | 12/2012 | Parker |
| 8,337,403 | B2 | 12/2012 | Al-Ali et al. |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,359,080 | B2 | 1/2013 | Diab et al. |
| 8,364,223 | B2 | 1/2013 | Al-Ali et al. |
| 8,364,226 | B2 | 1/2013 | Diab et al. |
| 8,374,665 | B2 | 2/2013 | Lamego |
| 8,385,995 | B2 | 2/2013 | Al-ali et al. |
| 8,385,996 | B2 | 2/2013 | Smith et al. |
| 8,388,353 | B2 | 3/2013 | Kiani et al. |
| 8,399,822 | B2 | 3/2013 | Al-Ali |
| 8,401,602 | B2 | 3/2013 | Kiani |
| 8,405,608 | B2 | 3/2013 | Al-Ali et al. |
| 8,414,499 | B2 | 4/2013 | Al-Ali et al. |
| 8,418,524 | B2 | 4/2013 | Al-Ali |
| 8,423,106 | B2 | 4/2013 | Lamego et al. |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,444,570 | B2 | 5/2013 | McGonigle et al. |
| 8,455,290 | B2 | 6/2013 | Siskavich |
| 8,457,703 | B2 | 6/2013 | Al-Ali |
| 8,457,707 | B2 | 6/2013 | Kiani |
| 8,463,349 | B2 | 6/2013 | Diab et al. |
| 8,466,286 | B2 | 6/2013 | Bellot et al. |
| 8,471,713 | B2 | 6/2013 | Poeze et al. |
| 8,473,020 | B2 | 6/2013 | Kiani et al. |
| 8,483,787 | B2 | 7/2013 | Al-Ali et al. |
| 8,489,364 | B2 | 7/2013 | Weber et al. |
| 8,498,684 | B2 | 7/2013 | Weber et al. |
| 8,504,128 | B2 | 8/2013 | Blank et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |

(56) References Cited

U.S. PATENT DOCUMENTS

| | | |
|---|---|---|
| 8,525,666 B2 | 9/2013 | Melker et al. |
| 8,529,301 B2 | 9/2013 | Al-Ali et al. |
| 8,529,459 B2 | 9/2013 | Malker et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,641,635 B2 | 2/2014 | Melker et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,679,028 B2 | 3/2014 | Melker et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,740,808 B2 | 6/2014 | Curti et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,857 B2 | 6/2014 | Melker et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,801,620 B2 | 8/2014 | Melker et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| D717,192 S | 11/2014 | Tanner et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,897,850 B2 * | 11/2014 | Jochim ............... A61B 5/6826 600/344 |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,155,826 B2 | 10/2015 | Ross et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,198,586 B2 | 12/2015 | Melker |
| 9,211,072 B2 | 12/2015 | Kiani |
| 9,211,095 B1 | 12/2015 | Al-Ali |
| 9,218,454 B2 | 12/2015 | Kiani et al. |
| D748,274 S | 1/2016 | Rich et al. |
| 9,226,696 B2 | 1/2016 | Kiani |
| 9,241,662 B2 | 1/2016 | Al-Ali et al. |
| 9,245,668 B1 | 1/2016 | Vo et al. |
| D748,774 S | 2/2016 | Caron |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |

(56) References Cited

U.S. PATENT DOCUMENTS

| | | |
|---|---|---|
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,370,634 B2 | 6/2016 | Melker et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,661 B2 | 6/2017 | Melker et al. |
| 9,668,679 B2 | 6/2017 | Schurman et al. |
| 9,668,680 B2 | 6/2017 | Bruinsma et al. |
| 9,668,695 B2 | 6/2017 | Melker |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,717,836 B2 | 8/2017 | Melker |
| 9,724,002 B2 | 8/2017 | Rich et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| D802,152 S | 11/2017 | Wakefield et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,950,112 B2 | 4/2018 | Melker et al. |
| 9,955,937 B2 | 5/2018 | Telfort |
| 9,965,946 B2 | 5/2018 | Al-Ali et al. |
| 9,974,479 B2 | 5/2018 | Melker |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| D844,793 S | 4/2019 | Dai |
| 10,279,247 B2 | 5/2019 | Kiani |
| 10,292,664 B2 | 5/2019 | Al-Ali |
| 10,299,720 B2 | 5/2019 | Brown et al. |
| 10,307,111 B2 | 6/2019 | Muhsin et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |

(56) References Cited

U.S. PATENT DOCUMENTS

| | | |
|---|---|---|
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2004/0230108 A1 | 11/2004 | Melker et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0078315 A1 | 4/2007 | Kling et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0092898 A1 | 4/2008 | Schneider et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0085527 A1 | 4/2010 | Konuma et al. |
| 2010/0085537 A1 | 4/2010 | Ramella-Roman et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0227740 A1 | 9/2011 | Wohltjen |
| 2011/0230733 A1 | 9/2011 | Al-Ali |
| 2011/0237969 A1 | 9/2011 | Eckerbom et al. |
| 2012/0078069 A1 | 3/2012 | Melker |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0272963 A1 | 11/2012 | Thomas et al. |
| 2012/0283524 A1 | 11/2012 | Kiani et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0005557 A1 | 1/2014 | Rich et al. |
| 2014/0012100 A1 | 1/2014 | Al-Ali et al. |
| 2014/0051953 A1 | 2/2014 | Lamego et al. |
| 2014/0081100 A1 | 3/2014 | Muhsin et al. |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275887 A1 | 9/2014 | Batchelder et al. |
| 2014/0275930 A1 | 9/2014 | Rich et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0343382 A1 | 11/2014 | Kersey et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0073233 A1 | 3/2015 | Rich et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0105632 A1 | 4/2015 | Melker et al. |
| 2015/0106121 A1 | 4/2015 | Muhsin et al. |
| 2015/0112151 A1 | 4/2015 | Muhsin et al. |

(56) References Cited

U.S. PATENT DOCUMENTS

| | | |
|---|---|---|
| 2015/0116076 A1 | 4/2015 | Al-Ali et al. |
| 2015/0126830 A1 | 5/2015 | Schurman et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0297137 A1 | 10/2015 | Welch et al. |
| 2015/0342480 A1 | 12/2015 | Kim et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366507 A1 | 12/2015 | Blank |
| 2015/0380875 A1 | 12/2015 | Coverston et al. |
| 2016/0029932 A1 | 2/2016 | Al-Ali |
| 2016/0051205 A1 | 2/2016 | Al-Ali et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0174855 A1 | 6/2016 | Deliwala |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224231 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0258403 A1 | 9/2017 | Abdul-Hafiz et al. |
| 2017/0311891 A1 | 11/2017 | Kiani et al. |
| 2018/0103874 A1 | 4/2018 | Lee et al. |
| 2018/0153446 A1 | 6/2018 | Kiani |
| 2018/0199871 A1 | 7/2018 | Pauley et al. |
| 2018/0213583 A1 | 7/2018 | Al-Ali |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |

FOREIGN PATENT DOCUMENTS

| | | |
|---|---|---|
| WO | WO 2005/065540 | 7/2005 |
| WO | WO 2018/194992 | 10/2018 |

OTHER PUBLICATIONS

International Search Report and Written Opinion for International Application No. PCT/US18/27833 dated Jul. 5, 2018 in 42 pages.

\* cited by examiner

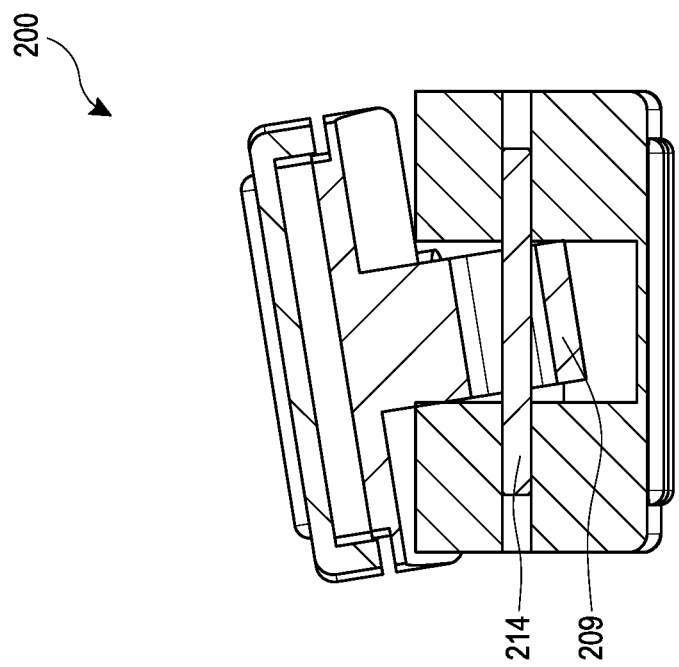
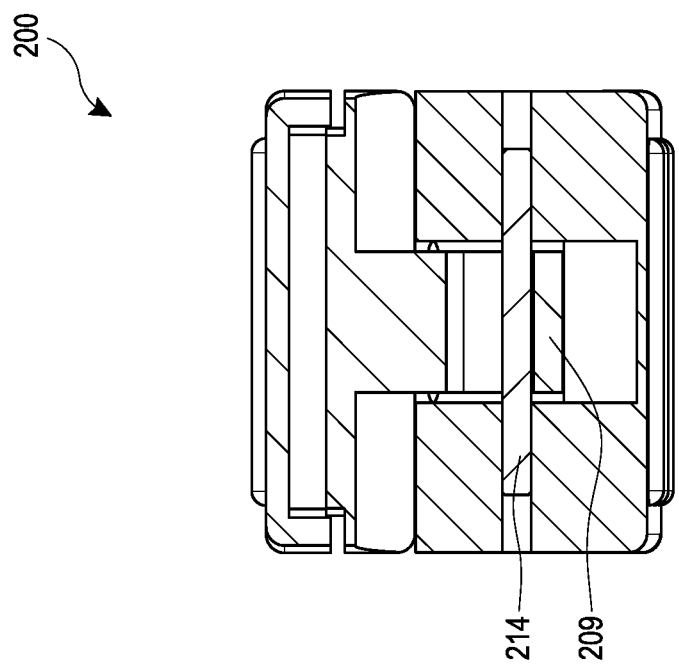
FIG. 7B
FIG. 7A

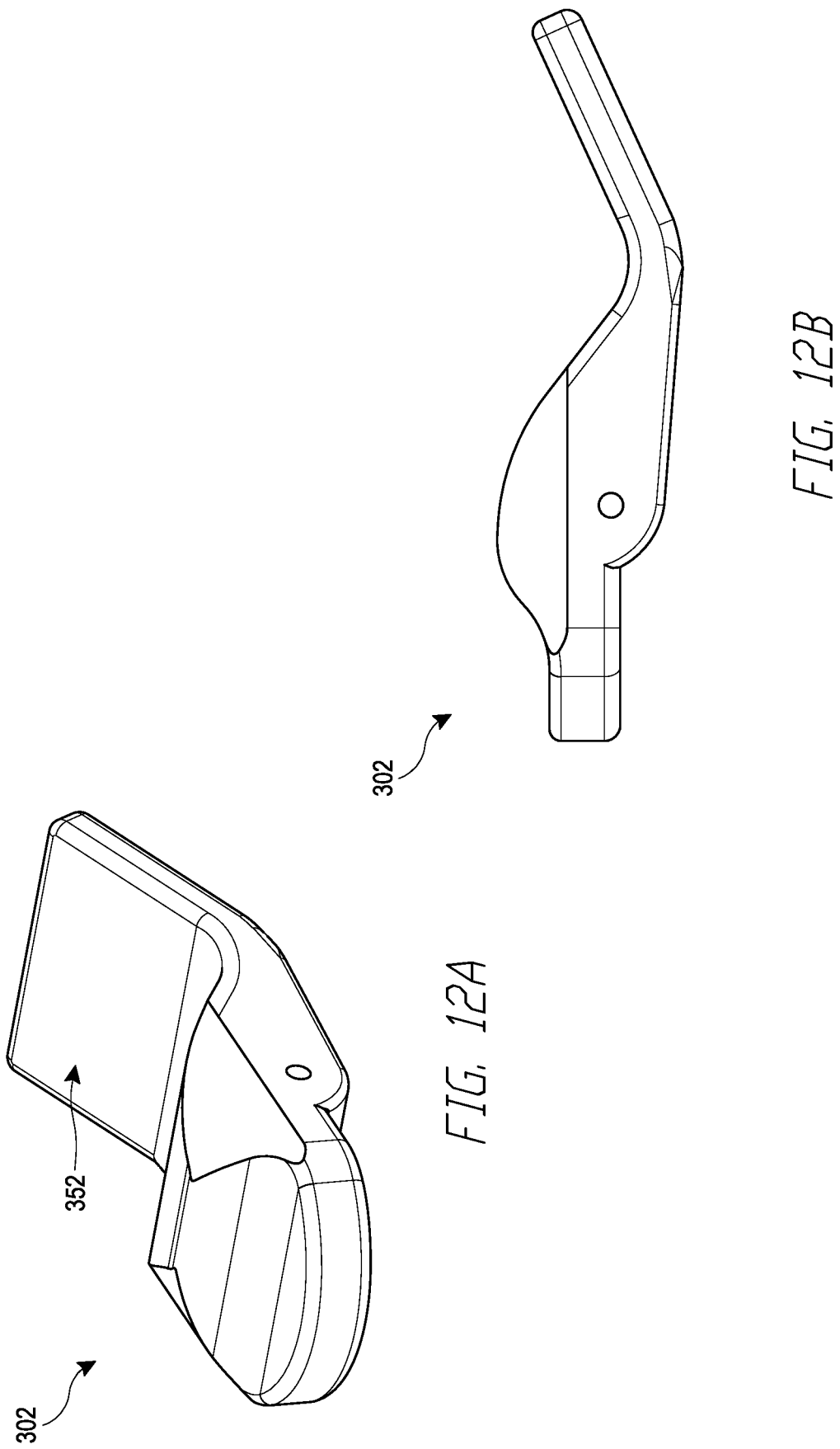

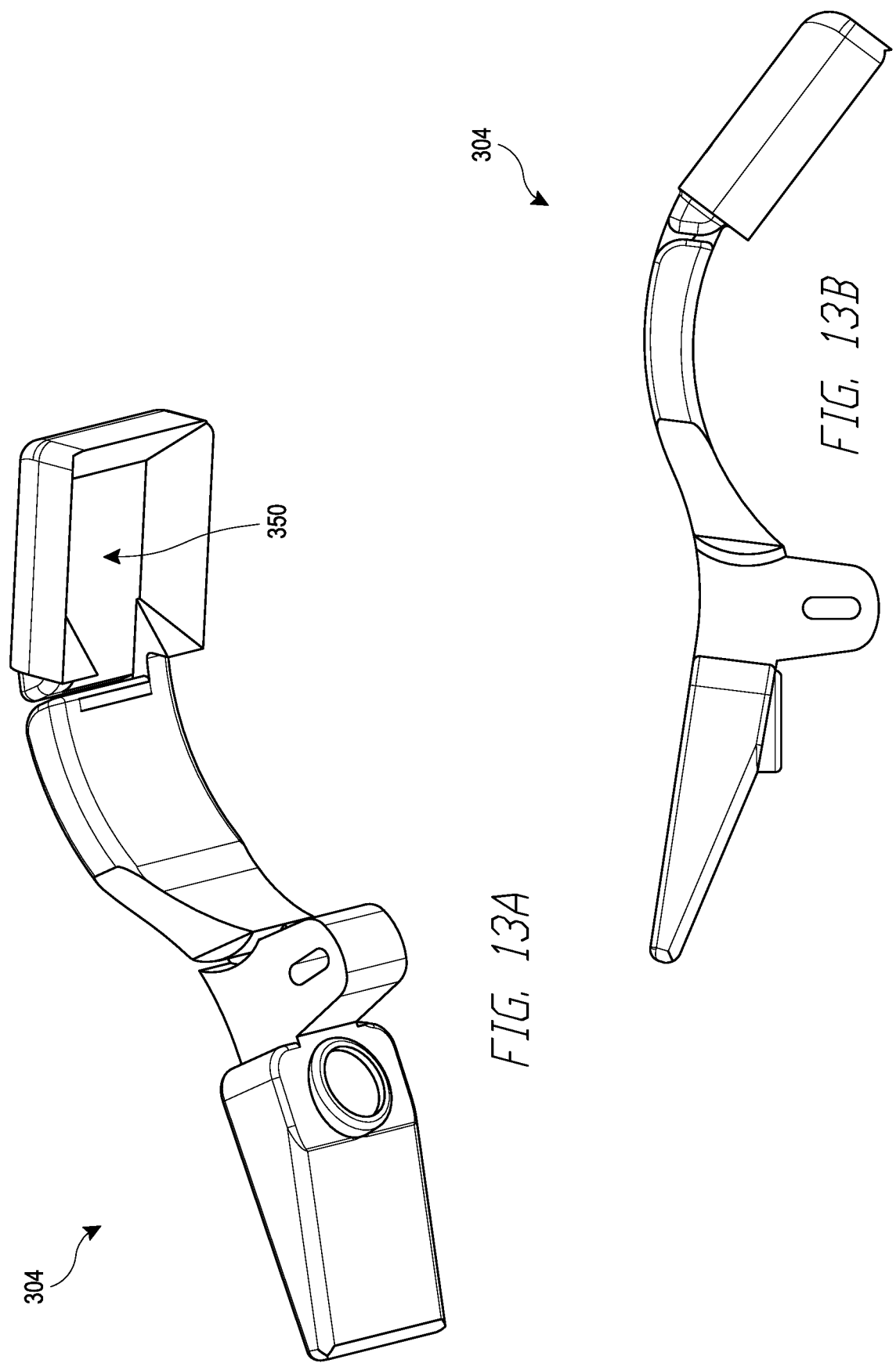

NOSE SENSOR

INCORPORATION BY REFERENCE TO ANY PRIORITY APPLICATIONS

This application is a continuation-in-part of U.S. patent application Ser. No. 15/451,288, filed Mar. 6, 2017, which is a continuation-in-part of U.S. patent application Ser. No. 15/448,971, filed Mar. 3, 2017, which claims the priority benefit under 35 U.S.C. § 119(e) of U.S. Provisional Application No. 62/303,743, filed Mar. 4, 2016, the entire contents of which are hereby incorporated by reference and should be considered a part of this specification. Any and all applications for which a foreign or domestic priority claim is identified in the Application Data Sheet as filed with the present application are hereby incorporated by reference under 37 C.F.R. § 1.57.

TECHNICAL FIELD

In general, the present disclosure relates to a wearable patient monitoring device, and methods and apparatuses for monitoring a patient's physiological information using the device. More specifically, the present disclosure relates to the connection of a patient monitoring device to a patient's nose.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters such as blood oxygen saturation level, respiratory rate, pulse, and a myriad of other parameters, such as those monitored on commercially available patient monitors from Masimo Corporation of Irvine, Calif. Clinicians, including doctors, nurses, and other medical personnel, use the physiological parameters and trends of those parameters obtained from patient monitors to diagnose illnesses and to prescribe treatments. Clinicians also use the physiological parameters to monitor patients during various clinical situations to determine whether to increase the level of medical care given to patients.

Examples of non-invasive patient monitoring devices include pulse oximeters. Pulse oximetry is a widely accepted noninvasive procedure for measuring the oxygen saturation level of arterial blood, an indicator of a person's oxygen supply. A pulse oximeter generally includes one or more light sources transmitting optical radiation into or reflecting off through a portion of the body, for example a digit such as a finger, a hand, a foot, a nose, an earlobe, or a forehead. After attenuation by tissue and fluids of the portion of the body, one or more photodetection devices detect the attenuated light and output one or more detector signals responsive to the detected attenuated light. The oximeter may, in various embodiments, calculate oxygen saturation ($SpO_2$), pulse rate, a plethysmograph waveform, perfusion index (PI), pleth variability index (PVI), methemoglobin (HbMet), carboxyhemoglobin (HbCO), total hemoglobin (HbT), glucose, and/or otherwise, and the oximeter may display on one or more monitors the foregoing parameters individually, in groups, in trends, as combinations, or as an overall wellness or other index. An example of such an oximeter, which can utilize an optical sensor described herein, are described in U.S. application Ser. No. 13/762,270, filed Feb. 7, 2013, titled "Wireless Patient Monitoring Device," U.S. application Ser. No. 14/834,169, filed Aug. 24, 2015, titled "Wireless Patient Monitoring Device," and U.S. application Ser. No. 14/511,974, filed Oct. 10, 2014, titled "Patient Position Detection System," the disclosures of which are hereby incorporated by reference in their entirety. Other examples of such oximeters are described in U.S. application Ser. No. 09/323,176, filed May 27, 1999, titled "Stereo Pulse Oximeter," now U.S. Pat. No. 6,334,065, the disclosure of which is hereby incorporated by reference in its entirety.

In noninvasive devices and methods, a sensor is often adapted to position a portion of the body proximate the light source and light detector. In one example, noninvasive sensors often include a clothespin-shaped finger clip that includes a contoured bed conforming generally to the shape of a finger. An example of such a noninvasive sensor is described in U.S. application Ser. No. 12/829,352, filed Jul. 1, 2010, titled "Multi-Stream Data Collection System for Noninvasive Measurement of Blood Constituents," now U.S. Pat. No. 9,277,880, the disclosure of which is hereby incorporated by reference in its entirety. In another example, noninvasive sensors can include one or more sensing components, such as the light source and/or the photodetectors on an adhesive tape, such as described in U.S. application Ser. No. 13/041,803, filed May 7, 2011, titled "Reprocessing of a physiological sensor," now U.S. Pat. No. 8,584,345, the disclosure of which is hereby incorporated by reference in its entirety.

The patient monitoring devices can also communicate with an acoustic sensor comprising an acoustic transducer, such as a piezoelectric element. The acoustic sensor can detect respiratory and other biological sounds of a patient and provide signals reflecting these sounds to a patient monitor. An example of such an acoustic sensor, which can implement any of the acoustic sensing functions described herein, is described in U.S. application Ser. No. 12/643,939, filed Dec. 21, 2009, titled "Acoustic Sensor Assembly," and in U.S. Application No. 61/313,645, filed Mar. 12, 2010, titled "Acoustic Respiratory Monitoring Sensor Having Multiple Sensing Elements," the disclosures of which are hereby incorporated by reference in their entirety. An example of such an acoustic sensor is also described in U.S. application Ser. Nos. 13/762,270, 14/834,169, and 14/511,974 referenced above.

SUMMARY

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as can be taught or suggested herein.

The present disclosure provides a noninvasive physiological monitoring device which can be configured to be secured to a nose of a patient. The device can include an upper sensor body including a recess; a lower sensor body; an emitter configured to be secured to an inner or outer wall of the patient by one of the upper sensor body or lower sensor body; and a joint configured to rotatably couple the upper sensor body to the lower sensor body. The emitter can include one or more light sources. The emitter can be an LED. The joint can include an upper joint, a first lower joint, a second lower joint, and a pin. The upper joint can include a slot, wherein the upper joint extends from the upper sensor body towards the lower sensor body. The first lower joint can comprise a pin hole, wherein the first lower joint can be positioned on a first side of the lower sensor body, and wherein the first lower joint extends from the lower sensor body towards the upper sensor body. The second lower joint can include a pin hole, wherein the second lower joint can be positioned on a second side of the lower sensor body, and wherein the second lower joint can extend from the lower sensor body towards the upper sensor body. The pin can be configured to extend through at least a portion of the slot of the upper joint and the pin hole of the first lower joint and the pin hole of the second lower joint. The upper joint can be positioned between the first lower joint and the second lower joint. The slot of the joint can allow the upper sensor body to rotate about a longitudinal axis of the device. The joint can prevent the upper sensor body from rotating about a transverse axis of the device. The transverse axis is perpendicular to the longitudinal axis.

The device can further include a biasing member coupled to a rear portion of the upper sensor body and a rear portion of the lower sensor body. The biasing member can be configured to space the upper sensor body from the lower sensor body. A front portion of the upper sensor body can be approximately parallel to a front portion of the lower sensor body in a neutral position.

The slot of the joint allows the upper sensor body to translate vertically along the slot relative to the lower sensor body. The device can further include a detector coupled to the emitter, wherein the detector has an interface output responsive to light emitted by the emitter and transmitted through tissue of the nose of the patient, wherein the detector generates a signal output. The device can further include a signal processor in communication with the interface output of the detector, the signal processor configured to generate a measurement of physiological parameters based on the signal output generated by the detector. The emitter can be positioned within the upper sensor body, and the noninvasive physiological monitoring device can further includes a diffuser which can optionally be positioned within the recess of the upper sensor body. The diffuser can be configured to diffuse light transmitted from the emitter into a portion of the nose of the patient. The noninvasive physiological monitoring device can include a lens configured to focus light into the detector. This combination allows the light from the emitters to be diffused into a greater amount of tissue and then focused back to the detector for detecting. This provides a more accurate measurement.

The lower sensor body can include a rear portion and a front portion, wherein an inner wall of the rear portion of the lower sensor body can be positioned closer to the upper sensor body than the front portion of the lower sensor body. The lower sensor body can include a rear portion, a front portion, and an intermediate portion transitioning between the rear portion and the front portion, the intermediate portion can be curved to conform to a shape of the nose of the patient. The lower sensor body can include a rear portion, a front portion, and an intermediate portion transitioning between the rear portion and the front portion, the intermediate portion can be inclined relative to the front portion to conform to a shape of the nose of the patient.

The lower sensor body can include a rear portion that is angled away from the upper sensor body. The upper sensor body can be parallel or generally parallel to a longitudinal axis of the device.

The present disclosure also provides a method of calculating a measurement of physiological parameters of a patient including transmitting light, by an emitter of a nose sensor, of at least first and second wavelengths through tissue of a nose of a patient; and determining the measurement of the physiological parameters, by the nose sensor, based on the output signal. The sensor can include an upper sensor body including a recess; a lower sensor body; a joint configured to rotatably couple the upper sensor body to the lower sensor body. The joint can include an upper joint, a first lower joint, a second lower joint, and a pin. The upper joint can include a slot, wherein the upper joint extends from the upper sensor body towards the lower sensor body. The first lower joint can include a pin hole, wherein the first lower joint can be positioned on a first side of the lower sensor body, and wherein the first lower joint extends from the lower sensor body towards the upper sensor body. The second lower joint can include a pin hole, wherein the second lower joint can be positioned on a second side of the lower sensor body, and wherein the second lower joint extends from the lower sensor body towards the upper sensor body. The pin can be configured to extend through at least a portion of the slot of the upper joint and the pin hole of the first lower joint and the pin hole of the second lower joint. The upper joint can be positioned between the first lower joint and the second lower joint. The slot of the joint can allow the upper sensor body to rotate about a longitudinal axis of the device. The joint can prevent the upper sensor body from rotating about a transverse axis of the device. The transverse axis can be perpendicular to the longitudinal axis. The emitter can be positioned within the upper sensor body and can be configured to be secured to an outer wall of the nose of the patient.

The method can further include detecting, by a detector of the nose sensor, light attenuated by the tissue of the nose of the patient; and generating an output signal, by the nose sensor, based on the light detected at the nose of the patient.

A diffuser can be positioned within the recess of the upper sensor body and the emitter can be positioned within the upper sensor body, the diffuser can be configured to diffuse light transmitted from the emitter into a portion of the nose of the patient. The method can further include focusing light attenuated by the tissue of the nose of the patient into the detector with a lens. The nose sensor can further include a biasing member coupled to a rear portion of the upper sensor body and a rear portion of the lower sensor body. The biasing member can be configured to space the upper sensor body from the lower sensor body.

The slot of the joint can allow the upper sensor body to translate vertically along the slot relative to the lower sensor body. The lower sensor body can include a rear portion and a front portion, an inner wall of the rear portion of the lower sensor body can be positioned closer to the upper sensor body than the front portion of the lower sensor body. The lower sensor body includes a rear portion, a front portion, and an intermediate portion transitioning between the rear portion and the front portion, wherein the intermediate portion can be curved to conform to a shape of the nose of the patient.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

FIG. 7A illustrates a front cross-sectional view of an embodiment of a nose sensor.

FIG. 7B illustrates a front cross-sectional view of an embodiment of a nose sensor.

FIG. 12A illustrates a perspective view of a lower sensor body of an embodiment of a nose sensor.

FIG. 12B illustrates a side view of a lower sensor body of an embodiment of a nose sensor.

FIG. 13A illustrates a perspective view of an upper sensor body of an embodiment of a nose sensor.

FIG. 13B illustrates a side view of an upper sensor body of an embodiment of a nose sensor.

DETAILED DESCRIPTION

Embodiments of the present disclosure will now be described with reference to the accompanying figures, wherein like numerals refer to like elements throughout. The following description is merely illustrative in nature and is in no way intended to limit the disclosure, its application, or uses. It should be understood that steps within a method may be executed in different order without altering the principles of the present disclosure. Furthermore, embodiments disclosed herein can include several novel features, no single one of which is solely responsible for its desirable attributes or which is essential to practicing the systems, devices, and methods disclosed herein.

General

This disclosure describes embodiments of noninvasive sensor systems that can enable a user to measure, view, compare, analyze and/or download information relating to the respiratory system, for example, via a computing device, which may contain more advanced functionality than traditional systems and devices. The computing device can be, for instance, a cellphone or smartphone, tablet, laptop, personal digital assistant (PDA), and/or the like.

Generally, the embodiments described herein can depict several example user interfaces that may be implemented in a user computing device. The user interfaces shown can depict example displays generated by the noninvasive sensor system and may be implemented in any of the user devices described herein.

The user interfaces shown may be implemented in a mobile application such as an application that runs on a mobile operating system such as the Android™ operating system available from Google™ or the iOS™ operating system available from Apple™. Alternatively, or in addition to being a mobile application, the user interfaces shown can be implemented in a web application that runs in a browser.

The user interfaces shown are merely examples that illustrate some example embodiments described herein and may be varied in other embodiments. For instance, user interface controls shown may include buttons, touch-selective components and the like which may be altered to include any type of user interface control including, but not limited to, checkboxes, radio buttons, select boxes, drop-down boxes, textboxes or any combination of the same. Likewise, the different user interface controls may be combined or their functionality may be spread apart amongst additional controls while retaining the similar or same functionality as shown and described herein. Although touchscreen interfaces are shown, other devices may implement similar user interfaces with other types of user input devices such as a mouse, keyboard, stylus, or the like.

Figure 1:
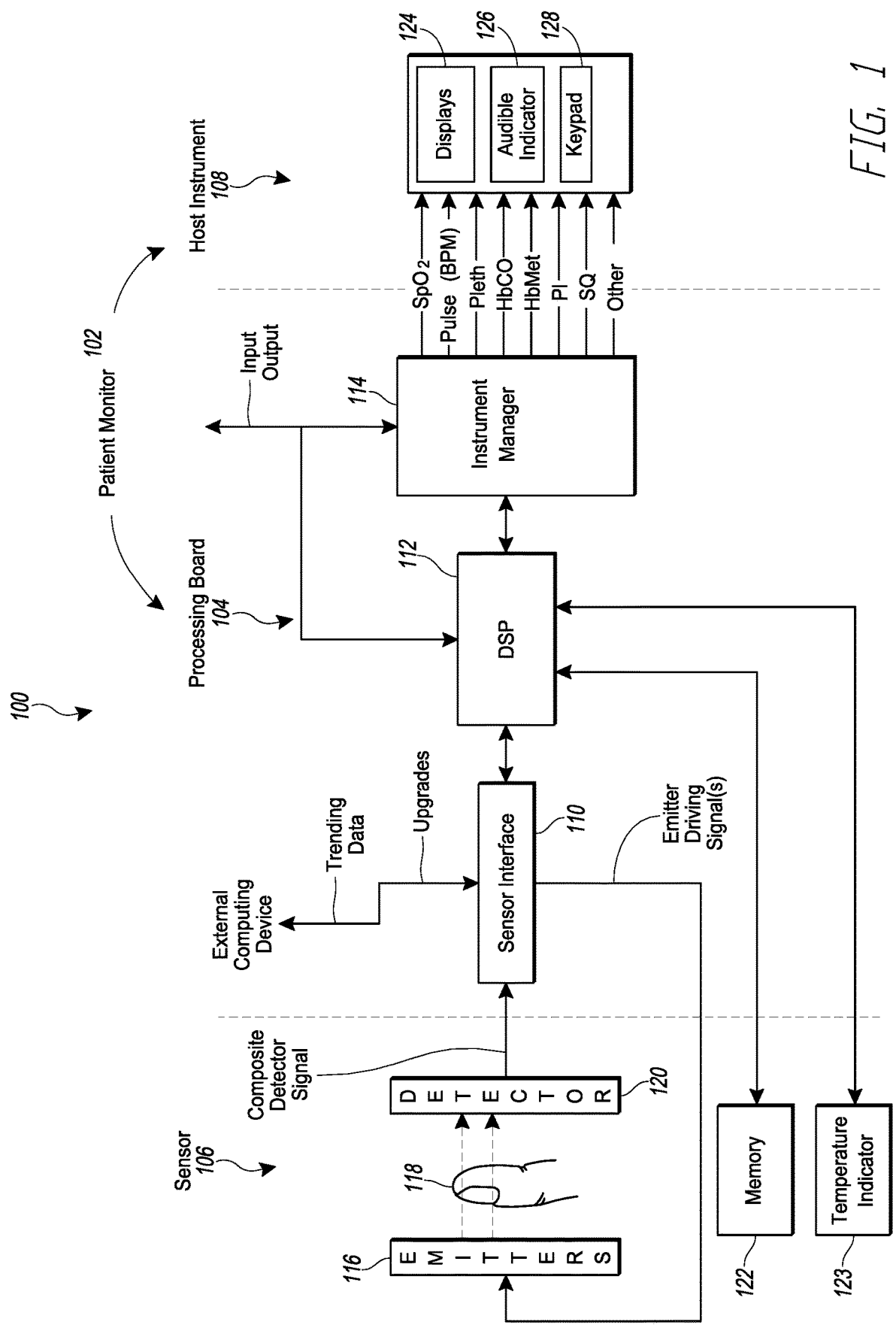
FIG. 1 illustrates a block diagram depicting one embodiment of a computer hardware system configured to run software for implementing one or more embodiments of the sensor system described herein.

FIG. 1 illustrates a block diagram of an exemplary embodiment of a user monitoring system 100. As shown in FIG. 1, the system 100 can include a user monitor 102 comprising a processing board 104 and a host instrument 108. The processing board 104 communicates with a sensor 106 to receive one or more intensity signal(s) indicative of one or more parameters of tissue of a user. The processing board 104 also communicates with a host instrument 108 to display determined values calculated using the one or more intensity signals. The processing board 104 can comprise processing circuitry arranged on one or more printed circuit boards capable of installation into the monitor 102, or capable of being distributed as some or all of one or more OEM components for a wide variety of host instruments monitoring a wide variety of user information. The processing board 104 can include a sensor interface 110, a digital signal processor and signal extractor ("DSP" or "processor") 112, and an instrument manager 114. In general, the sensor interface 110 converts digital control signals into analog drive signals capable of driving sensor emitters, and converts composite analog intensity signal(s) from light sensitive detectors into digital data.

The sensor interface 110 can manage communication with external computing devices. For example, a multipurpose sensor port (or input/output port) can connect to the sensor 106 or alternatively connecting to a computing device, such as a personal computer, a PDA, additional monitoring equipment or networks, or the like. When connected to the computing device, the processing board 104 may upload various stored data for, for example, off-line analysis and diagnosis. The stored data may comprise trend data for any one or more of the measured parameter data, plethysmograph waveform data acoustic sound waveform, or the like. Moreover, the processing board 104 may advantageously download from the computing device various upgrades or executable programs, may perform diagnosis on the hardware or software of the monitor 102. In addition, the processing board 104 may advantageously be used to view and examine user data, including raw data, at or away from a monitoring site, through data uploads/downloads, or network connections, combinations, or the like, such as for customer support purposes including software maintenance, customer technical support, and the like. Upgradable sensor ports are disclosed in U.S. Pat. No. 7,500,950, filed on Jul. 23, 2004, titled "Multipurpose Sensor Port," incorporated by reference herein.

As shown in FIG. 1, the digital data is output to the DSP 112. The DSP 112 can comprise a processing device based on the Super Harvard ARChitecture ("SHARC"), such as those commercially available from Analog Devices. However, a skilled artisan will recognize from the disclosure herein that the DSP 112 can comprise a wide variety of data and/or signal processors capable of executing programs for determining physiological parameters from input data. In particular, the DSP 112 includes program instructions capable of receiving multiple channels of data related to one or more intensity signals representative of the absorption (from transmissive or reflective sensor systems) of a plurality of wavelengths of emitted light by body tissue. The DSP 112 can accept data related to the absorption of eight (8) wavelengths of light, although an artisan will recognize from the disclosure herein that the data can be related to the absorption of two (2) to sixteen (16) or more wavelengths.

FIG. 1 also shows the processing board 104 including the instrument manager 114. The instrument manager 114 can comprise one or more microcontrollers controlling system management, including, for example, communications of calculated parameter data and the like to the host instrument 108. The instrument manager 114 may also act as a watchdog circuit by, for example, monitoring the activity of the DSP 112 and resetting it when appropriate.

The sensor 106 can comprise a reusable clip-type sensor, a disposable adhesive-type sensor, a combination sensor having reusable and disposable components, or the like. Moreover, an artisan will recognize from the disclosure herein that the sensor 106 can also comprise mechanical structures, adhesive or other tape structures, Velcro wraps or combination structures specialized for the type of user, type of monitoring, type of monitor, or the like. The sensor 106 can provide data to the board 104 and vice versa through, for example, a user cable. An artisan will also recognize from the disclosure herein that such communication can be wireless, over public or private networks or computing systems or devices, or the like. For example, such communication can be via wireless protocols such as Wi-Fi, Bluetooth, ZigBee, Z-wave, or radio frequency such as near field communication, or other wireless protocols such as cellular telephony infrared, satellite transmission, proprietary protocols, combinations of the same, and the like.

As shown in FIG. 1, the sensor 106 includes a plurality of emitters 116 irradiating the body tissue 118 with differing wavelengths of light, and one or more detectors 120 capable of detecting the light after attenuation by the tissue 118. The emitters 116 can include a matrix of eight (8) emission devices mounted on a flexible substrate, the emission devices being capable of emitting eight (8) differing wavelengths of light. The emitters 116 can comprise twelve (12) or sixteen (16) emitters, although other numbers of emitters are contemplated, including two (2) or more, three or more, four or more, five or more, six or more, or seven or more emitters, for example. As shown in FIG. 1, the sensor 106 may include other electrical components such as, for example, a memory device 122 comprising an EPROM, EEPROM, ROM, RAM, microcontroller, combinations of the same, or the like. Other sensor components may include an optional temperature determination device 123 or other mechanisms for, for example, determining real-time emission wavelengths of the emitters 116.

The memory 122 may advantageously store some or all of a wide variety data and information, including, for example, information on the type or operation of the sensor 106; type or identification of sensor buyer or distributor or groups of buyer or distributors, sensor manufacturer information, sensor characteristics including the number of emitting devices, the number of emission wavelengths, data relating to emission centroids, data relating to a change in emission characteristics based on varying temperature, history of the sensor temperature, current, or voltage, emitter specifications, emitter drive requirements, demodulation data, calculation mode data, the parameters for which the sensor is capable of supplying sufficient measurement data (e.g., HbCO, HbMet, HbT, or the like), calibration or parameter coefficient data, software such as scripts, executable code, or the like, sensor electronic elements, whether the sensor is a disposable, reusable, multi-site, partially reusable, partially disposable sensor, whether it is an adhesive or non-adhesive sensor, whether the sensor is a reflectance, transmittance, or transreflectance sensor, whether the sensor is a finger, hand, foot, forehead, or ear sensor, whether the sensor is a stereo sensor or a two-headed sensor, sensor life data indicating whether some or all sensor components have expired and should be replaced, encryption information, keys, indexes to keys or hash functions, or the like, monitor or algorithm upgrade instructions or data, some or all of parameter equations, information about the user, age, sex, medications, and other information that may be useful for the accuracy or alarm settings and sensitivities, trend history, alarm history, or the like. The monitor can advantageously store data on the memory device, including, for example, measured trending data for any number of parameters for any number of users, or the like, sensor use or expiration calculations, sensor history, or the like.

FIG. 1 also shows the user monitor 102 including the host instrument 108. The host instrument 108 can communicate with the board 104 to receive signals indicative of the physiological parameter information calculated by the DSP 112. The host instrument 108 preferably includes one or more display devices 124 capable of displaying indicia representative of the calculated physiological parameters of the tissue 118 at the measurement site. The host instrument 108 can advantageously include a handheld housing capable of displaying one or more of a pulse rate, plethysmograph data, perfusion quality such as a perfusion quality index ("PI™"), signal or measurement quality ("SQ"), values of blood constituents in body tissue, including for example, $SpO_2$, HbCO, HbMet, HbT, or the like. The host instrument 108 can display values for one or more of HbT, Hb, blood glucose, bilirubin, or the like. The host instrument 108 may be capable of storing or displaying historical or trending data related to one or more of the measured values, combinations of the measured values, plethysmograph data, or the like. The host instrument 108 also includes an audio indicator 126 and user input device 128, such as, for example, a keypad, touch screen, pointing device, voice recognition device, or the like.

The host instrument 108 can include audio or visual alarms that alert caregivers that one or more physiological parameters are falling below predetermined safe thresholds. The host instrument 108 can include indications of the confidence a caregiver should have in the displayed data. The host instrument 108 can advantageously include circuitry capable of determining the expiration or overuse of components of the sensor 106, including, for example, reusable elements, disposable elements, or combinations of the same.

Although described in terms of certain embodiments, other embodiments or combination of embodiments will be apparent to those of ordinary skill in the art from the disclosure herein. For example, the monitor 102 may comprise one or more monitoring systems monitoring parameters, such as, for example, vital signs, blood pressure, ECG or EKG, respiration, glucose, bilirubin, or the like. Such systems may combine other information with intensity-derived information to influence diagnosis or device operation. Moreover, the monitor 102 may advantageously include an audio system, preferably comprising a high quality audio processor and high quality speakers to provide for voiced alarms, messaging, or the like. The monitor 102 can advantageously include an audio out jack, conventional audio jacks, headphone jacks, or the like, such that any of the display information disclosed herein may be audiblized for a listener. For example, the monitor 102 may include an audible transducer input (such as a microphone, piezoelectric sensor, or the like) for collecting one or more of heart sounds, lung sounds, trachea sounds, or other body sounds and such sounds may be reproduced through the audio system and output from the monitor 102. Also, wired or wireless communications (such as Bluetooth™ or WiFi, including IEEE 801.11a, b, or g), mobile communications, combinations of the same, or the like, may be used to transmit the audio output to other audio transducers separate from the monitor 102. Other communication protocols can also be utilized. For example, such communication can be via wireless protocols such as ZigBee, Z-wave, or radio frequency such as near field communication, or other wireless protocols such as cellular telephony infrared, satellite transmission, proprietary protocols, combinations of the same, and the like.

Patterns or changes in the continuous noninvasive monitoring of intensity-derived information may cause the activation of other vital sign measurement devices, such as, for example, blood pressure cuffs.

Sensor System

This disclosure describes embodiments of patient monitoring devices that include one or more sensors and worn by a patient. For example, embodiments described herein and shown in the attached drawings include sensors and sensor systems for measuring physiological parameters. For example, sensors and physiological monitors described herein include hardware and/or software capable for determining and/or monitoring blood oxygenation levels in veins, arteries, a heart rate, a blood flow, respiratory rates, and/or other physiological parameters such as those discussed herein. For example, a pulse oximetry system may use an optical sensor clipped onto a patient's nose, for example, to measure a relative volume of oxygenated hemoglobin in pulsatile arterial blood flowing within, for example, the fingertip, foot, ear, forehead, or other measurement sites.

The monitoring device can be shaped and sized for use in various environmental settings and for use in various applications. For example, as described above, using the nose sensor, a medical patient can be monitored using one or more sensors, each of which can transmit a signal over a cable or other communication link, protocol, or medium such as those discussed herein to a physiological monitor. A nose sensor can be placed on the alar region of the nose. As referred to herein, "nose" can include to any portion of a patient's nose. For example, the patient's nose can include at least a portion of the patient's nostril, the alar region of the nose, an inner surface of the nose, and/or an outer surface of the nose, among other portions. As described above, the nose sensor can measure internal and/or external carotid arteries, veins, and/or other vessels to determine blood oxygenation levels and/or changes, heart rates, blood flow measurements, respiratory rates, other physiological parameters such as those discussed herein and/or the like.

Figure 2A:
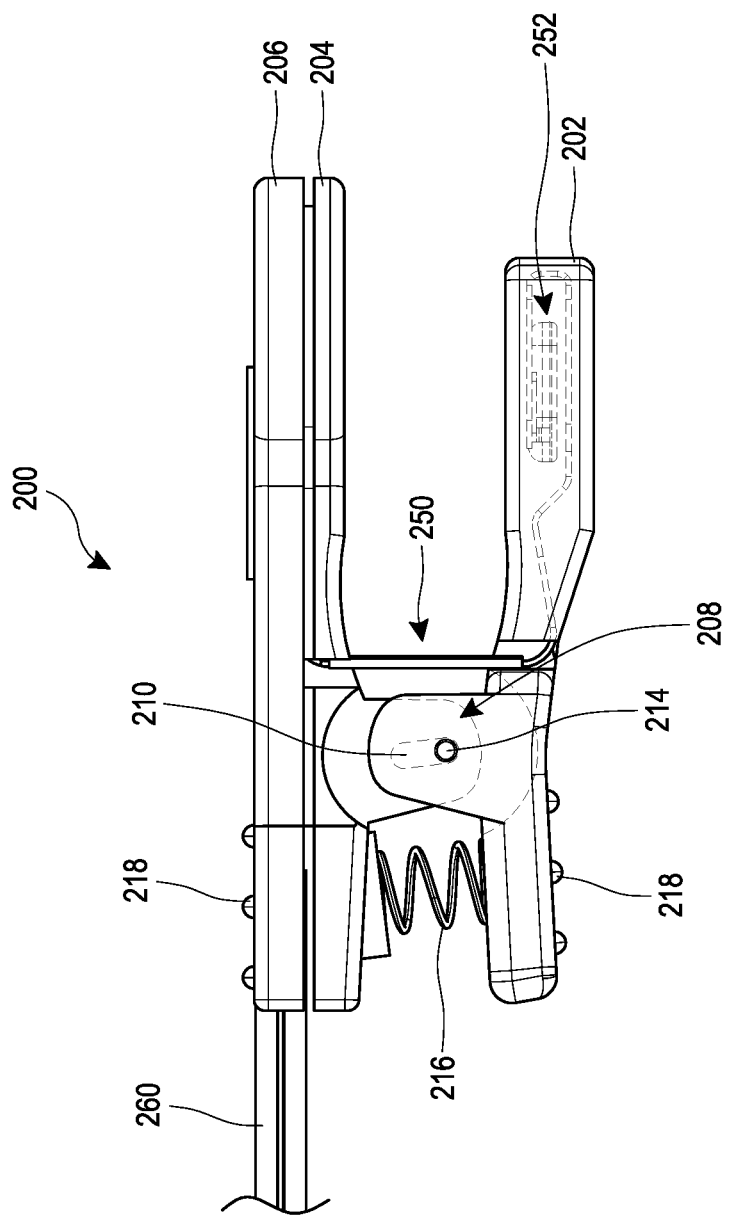
FIG. 2A illustrates an embodiment of a nose sensor.
Figure 3:
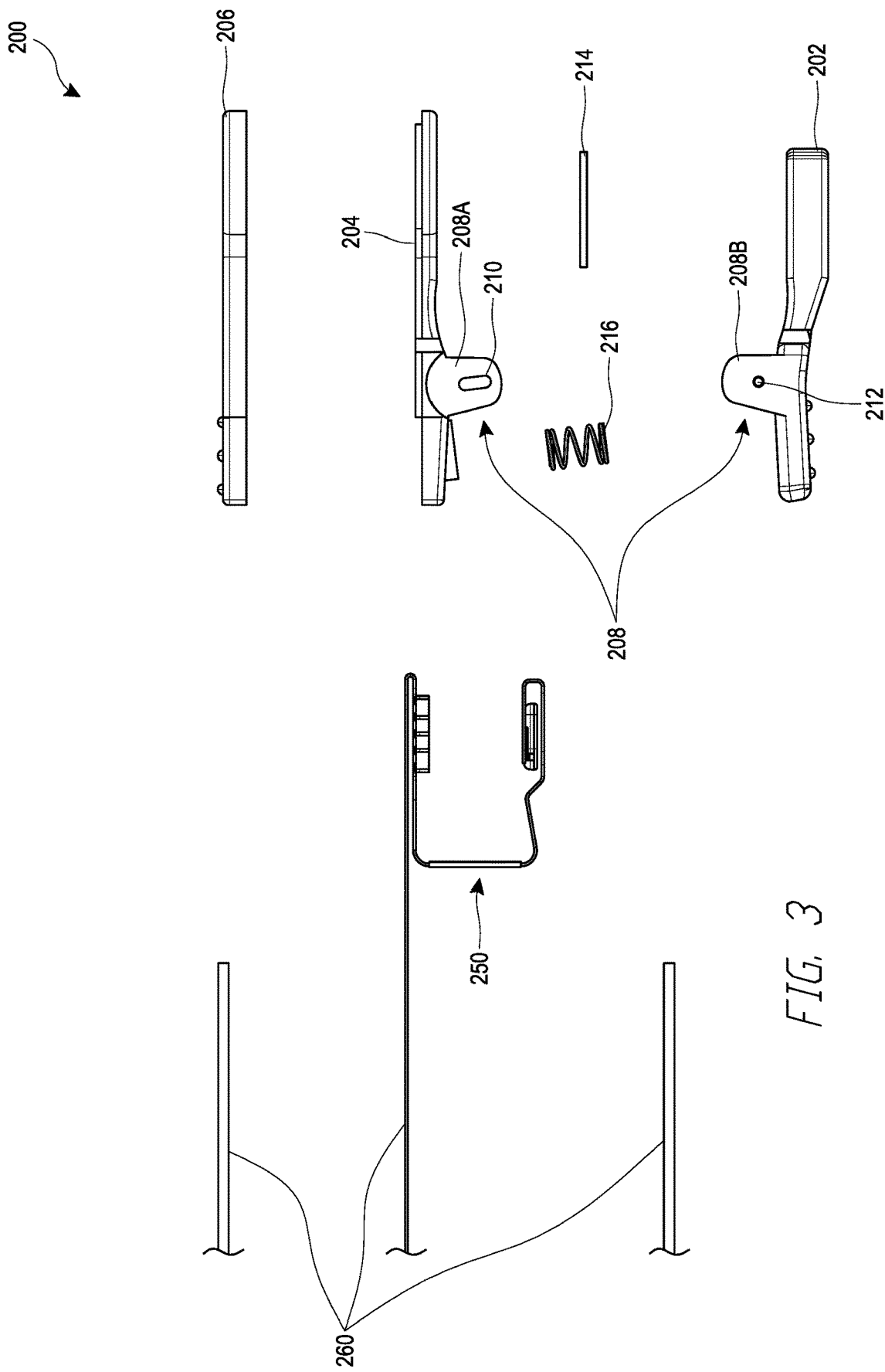
FIG. 3 illustrates an exploded view of an embodiment of a nose sensor.
Figure 4A:
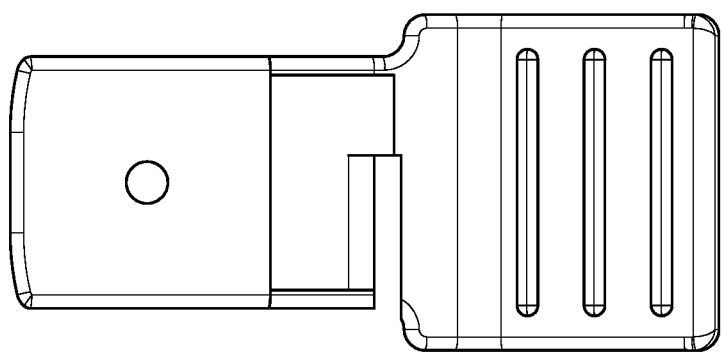
FIG. 4A illustrates a bottom view of a lower sensor body of an embodiment of a nose sensor.
Figure 4B:
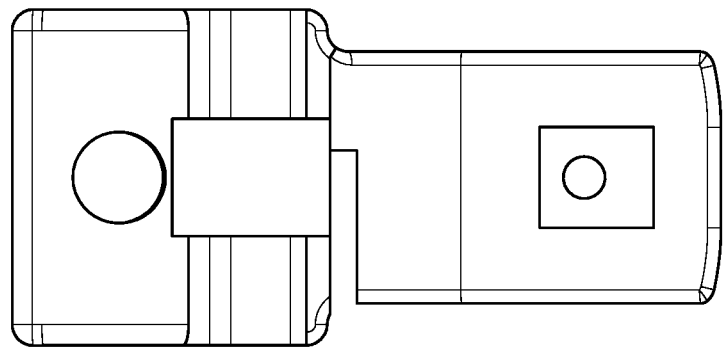
FIG. 4B illustrates a top view of a lower sensor body of an embodiment of a nose sensor.
Figure 4C:
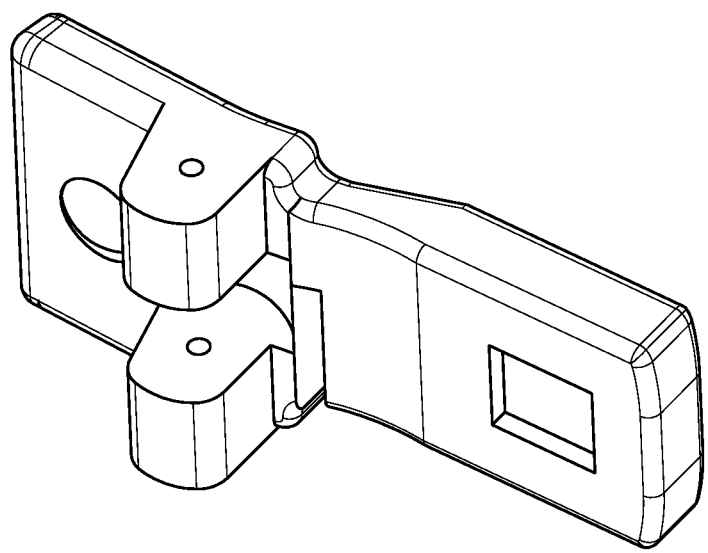
FIG. 4C illustrates a bottom perspective view of a lower sensor body of an embodiment of a nose sensor.
Figure 5A:
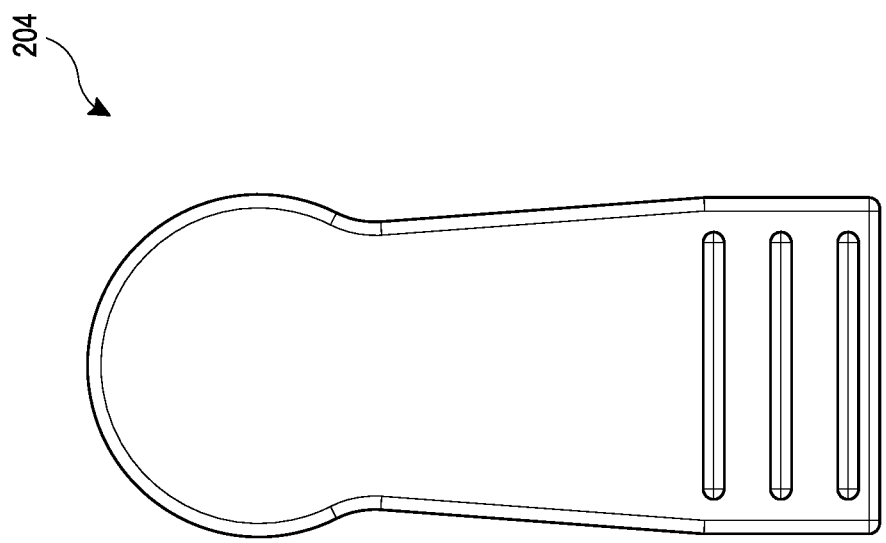
FIG. 5A illustrates a top view of an upper sensor body of an embodiment of a nose sensor.
Figure 5B:
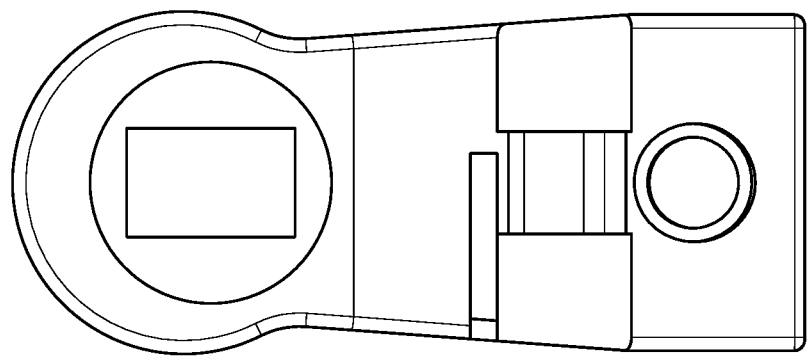
FIG. 5B illustrates a bottom view of an upper sensor body of an embodiment of a nose sensor.

The nose sensor can also include sensing elements such as, for example, acoustic piezoelectric devices, electrical ECG leads, pulse oximetry sensors, and/or the like. The sensors can generate respective signals by measuring one or more physiological parameters of the patient. The signals can then be processed by one or more processors. The one or more processors then can communicate the processed signal to a display if a display is provided. The display can be incorporated in the physiological monitor. The display can be separate from the physiological monitor. In some configurations, nose sensor can have one or more cables connecting the sensor to a monitor, other sensors, and/or a display, among other components As shown in FIGS. 2A-3 the nose sensor 200 can include an upper sensor body 204, a lower sensor body 202, and a cover 206. FIGS. 5A-5B illustrate the upper sensor body 204. FIGS. 4A-4C illustrate the lower sensor body 202. The upper sensor body 204 can be rotatably coupled to the lower sensor body 202 by a joint 208. As described in more detail below, the joint 208 can include an upper joint 208A and a lower joint 208B (see FIG. 3). The upper joint 208A can extend outwardly from the upper sensor body 204 and the lower joint 208B can extend outwardly from the lower sensor body 202 such that when assembled, upper joint 208A extends towards the lower sensor body 202 and the lower joint 208B extends towards the upper sensor body 204. The lower sensor body 202 can include one or more lower joints 208B, such as two or more, three or more, or four or more lower joints 208B, for example. As described in more detail below and as shown in the figures, the lower sensor body 202 can include at least two lower joints 208B that extend from opposite sides of the lower sensor body 202. The upper sensor body 204 can include one or more upper joints 208A, such as two or more, three or more, or four or more upper joints 208A, for example. As described in more detail below, the upper sensor body 204 can include at least one upper joint 208A positioned approximately at a center of the upper sensor body 204 such that the upper joint 208A is configured to be positioned between the lower joints 208B when assembled. For example, the upper sensor body 204 can include one upper joint 208A positioned approximately at a center of the upper sensor body 204 and configured to be positioned between two lower joints 208B when assembled.

As shown in FIG. 3, the nose sensor 200 can include a flex circuit 250 that connects the emitter and detector, such as the emitters and detectors discussed herein. The flex circuit 250 can be bendable. Alternatively, the flex circuit 250 can be substantially non-bendable or stiff. The flex circuit 250 can comprise various materials including but not limited to plastic and/or silicone. The flex circuit 250 can be a printed circuit board, for example.

The nose sensor 200 can be configured in a clip-type arrangement. Such an arrangement can allow the nose sensor 200 to be secured to (for example, clipped onto) a patient's nose. For example, the nose sensor 200 can be secured to the alar region of the patient's nose, among other portions. While the nose sensor 200 can have a generally clip-type arrangement, other arrangements are also contemplated.

As shown in FIG. 2A, the upper sensor body 204 can be spaced apart from the lower sensor body 202 by a biasing member 216. The biasing member 216 can include a spring, rubber material, and/or a compressible material, for example. Accordingly in a neutral position (for example as illustrated in, FIG. 2A), a rear portion of the upper sensor body 204 can be spaced apart from a rear portion of the lower sensor body 202. In such configurations, in a neutral position, a front portion of the upper sensor body 204 can be approximately parallel to a front portion of the lower sensor body 202. In a neutral position, side walls of the lower sensor body 202 can be generally parallel to side walls of the upper sensor body 204. In the neutral position, the rear portion of the lower sensor body 202 can be angled away from the upper sensor body 204. In the neutral position, the rear portion of the lower sensor body 202 can be angled towards from the upper sensor body 204. In the neutral position, the rear portion of the lower sensor body 202 can be approximately parallel to the upper sensor body 204.

The rear portion and front portion of the lower sensor body 202 can be connected by an intermediate portion. Generally, the rear portion, intermediate portion, and the front portion of the lower sensor body 202 are integrally formed. The rear portion can smoothly transition to the front portion along the intermediate portion. Generally, the intermediate portion can be curved and/or inclined. For example, as shown in FIG. 2A, in the neutral position, a bottom surface of the rear portion of the lower sensor body 202 can be positioned above a bottom surface of the front portion of the lower sensor body 202. All or a portion of a top surface of the rear portion of the lower sensor body 202 can be positioned above all or a portion of a top surface of the front portion of the lower sensor body 202.

The upper sensor body 204 can be generally flat and/or straight. For example, the upper sensor body 204 may not include a curved and/or included intermediate portion. A front portion, a rear portion, and an intermediate portion of the upper sensor body 204 can be approximately aligned.

Such configurations of the nose sensor 200 described herein can advantageously conform to the inner and/or outer walls of the patient's nose and/or can accommodate various nose shapes and/or sizes. For example, in use, at least the front portion of the lower sensor body 202 can be configured to be inserted into a patient's nose and engage an inner side wall of the patient's nose. In such configurations, at least the front portion of the upper sensor body 204 can be configured to remain outside of the patient's nose and secure the nose sensor 200 to the patient along an outer wall of the patient's nose. The general curvature and/or shape of the nose sensor can allow the nose sensor 200 to easily accommodate various nose shapes and sizes. For example, the shape of the intermediate region of the lower sensor body 202 can conform to an inner surface of the patient's nose. Such configurations allow the nose sensor 200 to maintain a low profile and/or thickness. This can reduce the overall bulkiness of the sensor 200. Accordingly, the nose sensor 200 can be relatively lightweight and take up less space when secured to the patient. Thus, the nose sensor 200 can be less obtrusive and/or have enhanced aesthetics.

As shown in at least FIGS. 2A and 3, the nose sensor 200 can include a biasing member 216. The biasing member 216 can include a compression spring, among other materials described herein. Where the biasing member 216 comprises a compression spring, the spring can comprise various strength and/or stiffness properties, and/or other material properties.

The biasing member 216 can be in contact with or be coupled to the upper sensor body 204 and/or the lower sensor body 202. For example, the upper sensor body 204 can include a protrusion and/or recess for receiving one end of the biasing member 216. The upper sensor body 204 can include a skirt wall extending around a perimeter of an interior surface of the upper sensor body 204 which can help secure and/or align the biasing member 216. The biasing member 216 can be adhered to the inner surface of the upper sensor body 204. As discussed above, the biasing member 216 can space the upper sensor body 204 from the lower sensor body 202. The lower sensor body 202 can include a protrusion and/or recess for receiving one end of the biasing member 216. The lower sensor body 202 can include a skirt wall extending around a perimeter of an interior surface of the lower sensor body 202 which can help secure and/or align the biasing member 216. The biasing member 216 can adhered to the inner surface of the lower sensor body 202. The biasing member 216 can be adhered to the inner surface of the lower sensor body 202 and the inner surface of the upper sensor body 204.

The biasing member 216 can be positioned at an approximate center of the nose sensor 200 along a longitudinal axis of the nose sensor 200 that extends from a front portion of the nose sensor 200 to a rear portion. For example, the biasing member 216 can be positioned at an approximate center of a width of the nose sensor 200 between lateral sides of the nose sensor 200.

The biasing member 216 can be positioned at the rear portion of the nose sensor 200. Such configurations can provide a symmetric restoring force, which can bias the nose sensor to the neutral position, as discussed herein.

Figure 2B:
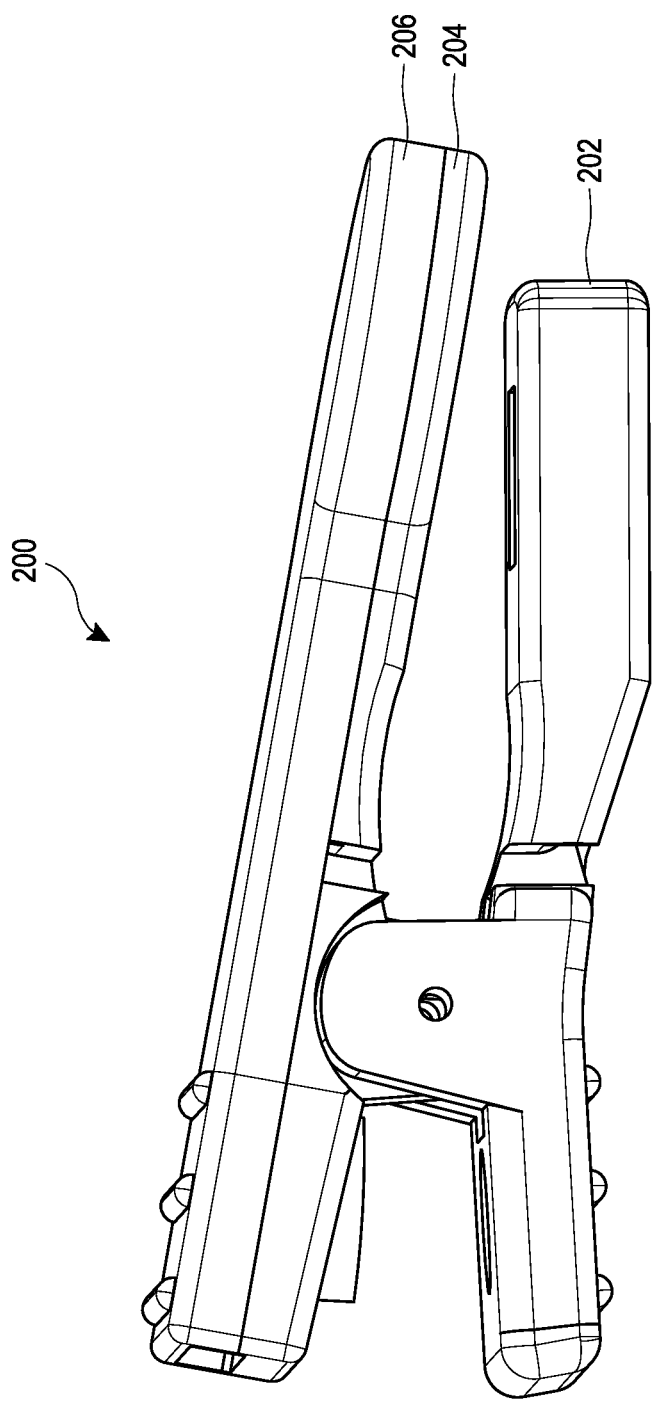
FIG. 2B illustrates an embodiment of a nose sensor.

FIG. 2B illustrates an assembly of the nose sensor 200. As shown, when no biasing member 216 is coupled to the rear portion of the nose sensor 100, the front portion of the upper sensor body 204 and/or the lower sensor body 202 can rotate about the pin 214 towards one another.

When no or minimal external forces are applied to the nose sensor 200, the biasing member 216 can be not compressed or expanded and/or can be minimally compressed and/or minimally expanded. As shown in at least FIG. 2A, in the neutral position, a rear portion of the upper sensor body 204 can be spaced apart from a rear portion of the lower sensor body 202. In a neutral position, a front portion of the upper sensor body 204 can be approximately parallel to a front portion of the lower sensor body 202. In a neutral position, side walls of the lower sensor body 202 can be generally parallel to side walls of the upper sensor body 204. In the neutral position, the rear portion of the lower sensor body 202 can be angled away from the upper sensor body 204.

When a force is applied to the biasing member 216, such as when an external force is applied to the nose sensor 200 to open the clip-type arrangement, the biasing member 216 can allow the upper sensor body 204 to rotate about the pin 214 relative to the lower sensor body 202 and/or the lower sensor body 202 to rotate about the pin 214 relative to the upper sensor body 204. When an external force is applied to the nose sensor 200, the biasing member 216 can allow the upper sensor body 204 to rotate and/or tilt about the longitudinal axis of the nose sensor 200 relative to the lower sensor body 202, and/or the lower sensor body 202 to rotate and/or tilt about the longitudinal axis of the nose sensor 200 relative to the upper sensor body 204. The biasing member 216 can bias the upper sensor body 204 and/or the lower sensor body 202 to the neutral position, in which no and/or minimal external forces are applied. Thus, the biasing member 216 can allow the nose sensor 200 to comfortably be secured to a patient's nose. For example, the biasing member 216 can bias the lower sensor body 202 towards the wall of the patient's nose in use and/or the upper sensor body 204 towards the patient's nose in use.

The biasing member 216 can be coupled to a rear portion of the upper sensor body 204 and the lower sensor body 202. For example, the biasing member 216 can be positioned rear of the joint 208, as shown in at least FIG. 2A. Thus, the biasing member 216 can space the upper sensor body 204 from the lower sensor body 202. As shown in at least FIG. 2A, for example, this can allow a greater range of rotation about the joint 208. Such configurations can allow for the nose sensor 200 to accommodate a greater variety of nose shapes and sizes.

The biasing member 216 can act to bias the clip-type arrangement of the nose sensor 200 towards a neutral position. Such configurations can allow the joint 208 to be biased in various arrangements to accommodate different shaped and/or sized noses. For example, if the biasing member 216 acts behind the joint, as shown, the joint 208 can be biased in an upwards direction to accommodate larger-sized noses. The biasing member 216 can be positioned in front of the joint 208. In such configurations, the joint 208 can be biased in a downwards direction to accommodate smaller-sized noses.

As shown in FIGS. 2A and 2B the nose sensor 200 can include a joint 208. The joint 208 can include a prismatic joint, among other configurations. The joint 208, alone, or in combination with the biasing member 216, can form a hinge-like configuration to allow the nose sensor to be opened and/or closed. The joint 208 can include a pin 214 positioned within a pin hole 212 and a slot 210.

As described above, the prismatic joint 208 can include an upper joint 208A and a lower joint 208B. The upper joint 208A can extend outwardly from a side wall of the upper sensor body 204 at an angle approximately perpendicular to an outer wall of the upper sensor body 204. The upper joint 208A can extend outwardly from a side wall of the upper sensor body 204 at an angle that is not perpendicular to the outer wall of the upper sensor body 204. For example, the upper joint 208A can extend outwardly from a side wall of the upper sensor body 204 at an angle slightly more than 90 degrees with reference to an outer wall of the upper sensor body, or at an angle of 100 degrees, 110 degrees, 120 degrees, 130 degrees, 140 degrees, 150 degrees, 160 degrees, 170 degrees, or any value therebetween, or any range bounded by any combination of these values, although values outside these ranges can be used in some cases. The upper sensor body 204 can include the upper joint 208A on one or both sides of the upper sensor body 204, or can include the upper joint 208A in between sides of the upper sensor body 204. The upper joint 208A can include a slot 210.

The lower joint 208B can extend outwardly from a side wall of the lower sensor body 202 at an angle approximately perpendicular to an outer wall of the lower sensor body 202. The lower joint 208B can extend outwardly from a side wall of the lower sensor body 202 at an angle that is not perpendicular to the outer wall of the lower sensor body 202. For example, the lower joint 208B can extend outwardly from a side wall of the lower sensor body 202 at an angle slightly more than 90 degrees with reference to an outer wall of the upper sensor body, or at an angle of 100 degrees, 110 degrees, 120 degrees, 130 degrees, 140 degrees, 150 degrees, 160 degrees, 170 degrees, or any value therebetween, or any range bounded by any combination of these values, although values outside these ranges can be used in some cases. The lower sensor body 202 can include the lower joint 208B on one or both sides of the lower sensor body 202, or can include the lower joint 208B in between sides of the lower sensor body 202.

The lower joint 208B can include a pin hole 212. The pin hole 212 can be configured to receive a pin 214. For example, the pin 214 can include an axis of rotation extending through the pin 214 to allow the nose sensor 200 to rotate from the neutral position to an open position (for example, when the front portion of the upper sensor body 204 and the lower sensor body 202 rotate away from one other), the neutral position to a closed position (for example, when the front portion of the upper sensor body 204 and the lower sensor body 202 rotate about the axis of rotation towards one other), from the open position to the neutral position, from the closed position to the neutral position, from the closed position to the open position, and/or from the open position to the closed position.

The pin 214 can be configured to slide through the pin hole 212. The pin 214 can be fixed and/or otherwise retained within the pin hole 212. The pin 214 can be arranged to rotationally couple the upper sensor body 204 to the lower sensor body 202, alone, or in combination with other features of the nose sensor 200. For example, the pin 214 can be configured to slide through the slot 210 formed in the upper joint 208A of the upper sensor body 204. The pin 214 can be locked into place within the slot 210. The slot 210 can allow for enhanced comfort to the patient when worn. For example, the slot 210 can allow the nose sensor 200 to accommodate a larger range of nose shapes and sizes. Depending on the size and/or shape of the patient's nose, the pin 214 can translate from a first end of the slot 210 to a second end of the slot 210 such that the upper sensor body 204 can be spaced laterally closer to and/or farther away from the lower sensor body 202. The pin 214 can be locked into place at a position spaced from the first end and/or the second end of the slot 210.

The joint 208 can advantageously allow motion about an axis of rotation extending though the pin 214. The joint 208 can advantageously allow movement about the longitudinal axis of the sensor 200 (e.g., an axis extending from a front end to a rear end). The joint 208 can advantageously allow movement about the longitudinal axis of the sensor 200 and/or the rotational axis of the pin 214. The longitudinal axis of the sensor 200 is perpendicular to the rotational axis of the pin 214.

Such configurations can allow the nose sensor to accommodate various nose sizes and shapes. This improves comfort of wearing the nose sensor when worn. For example, the patient can wear the sensor comfortably with minimal adjustment once the sensor is attached to the patient's nose.

Figure 6B:
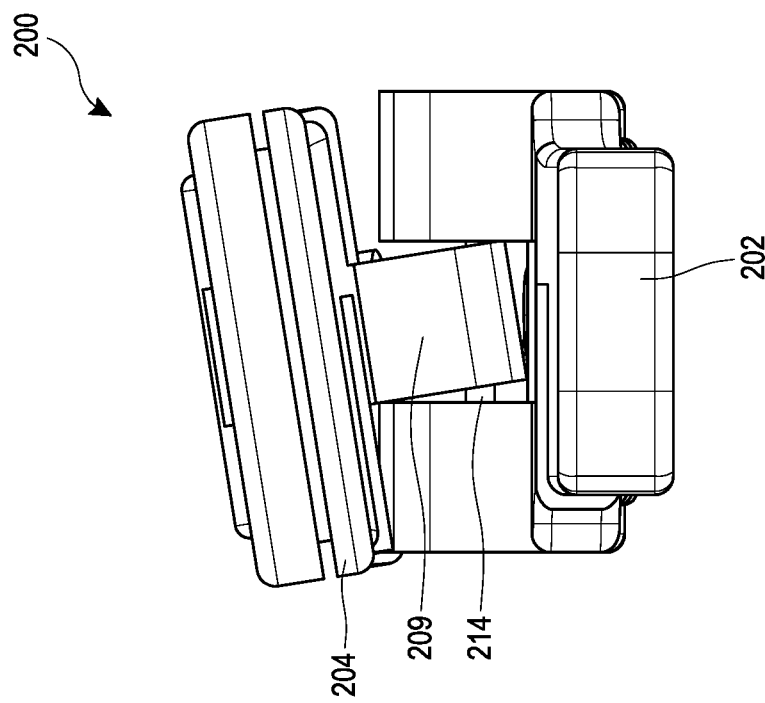
FIG. 6B illustrates a front view of an embodiment of a nose sensor.
Figure 6A:
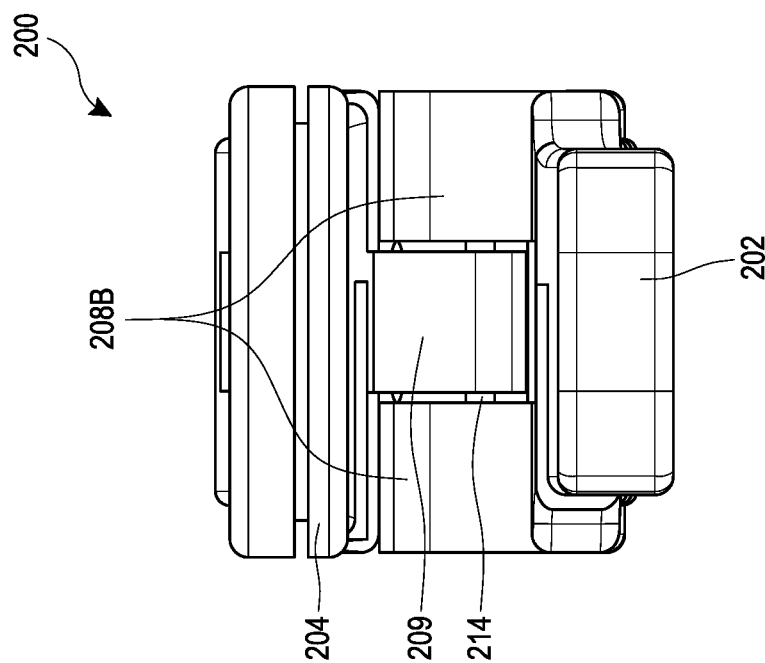
FIG. 6A illustrates a front view of an embodiment of a nose sensor.

FIGS. 6A and 6B illustrate an embodiment of the nose sensor 200. As shown in FIGS. 6A and 6B, the lower sensor body 202 can include two lower joints 208B. For example, the pin 214 can be configured to extend from a first lower joint to a second lower joint positioned on an opposite lateral side of the lower sensor body 202.

The slot 210 can be formed in a tongue 209 (see e.g., FIG. 3). The tongue 209 can be integrally formed with and/or coupled to the upper sensor body 204. The tongue 209 can be positioned approximately at a center between side walls of the upper sensor body 204 and extends from a bottom surface of the upper sensor body 204. Accordingly, the tongue 209 can be positioned between the first and second lower joints 208B when assembled. Such configurations can limit lateral movement of the upper sensor body 204 relative to the lower sensor body 202.

FIG. 6B illustrates the upper sensor body 204 tilted relative to the lower sensor body 202. The slot 210 formed in the tongue 209 can allow the upper sensor body 204 to tilt from one side to the other relative to the lower sensor body 202. The top wall of the lower joint 208B can limit the extent of the tilt. For example, the top wall of the lower joint 208B can limit the amount of rotation of the upper sensor body 204 about the longitudinal axis of the nose sensor 200 such that the top wall of the lower joint 208B acts as a stopper to limit rotation. The lower joint 208B can be raised at various lengths to allow a lesser and/or greater amount of rotation about the longitudinal axis of the nose sensor 200.

The tongue 209 can entirely enclose the pin 214 when assembled. For example, the tongue 209 can be configured to prevent the pin from translating in a forward-rearward direction, but allows the pin to translate in an upwards-downwards direction. The tongue 209 at least partially encloses the pin 214. For example, the tongue 209 may only partially wrap around the pin 214 (for example, hook around) such that the upper sensor body 204 can be easily disassembled and/or detached from the lower sensor body 202.

FIGS. 7A and 7B illustrate cross-sectional views of an embodiment of the nose sensor 200. For example, FIG. 7A illustrates an example of a cross-sectional view of the sensor device 200 in a neutral position. FIG. 7B illustrates an example of a cross-sectional view of the sensor device 200 in a titled position. The pin 214 can extend through the pin hole 212 formed in the lower joints 208B and the slot 210 formed in the tongue 209 to rotatably connect the upper sensor body 204 to the lower sensor body 202.

Figure 8B:
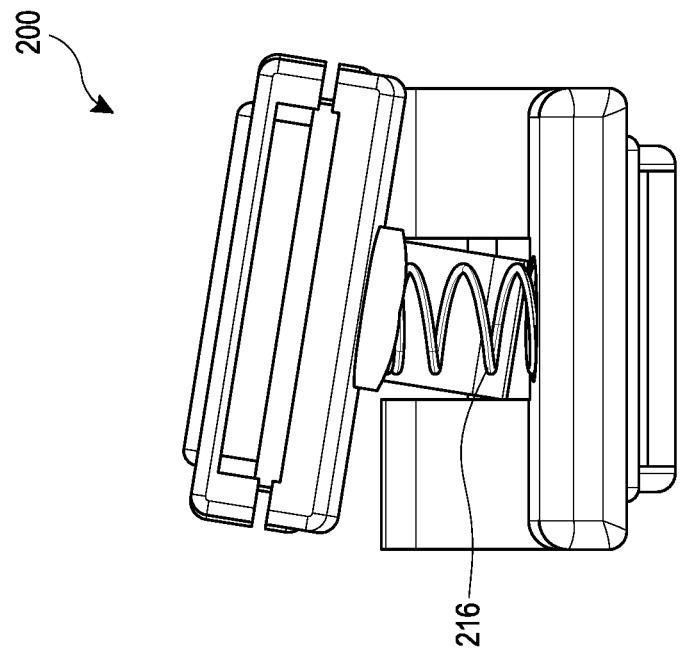
FIG. 8B illustrates a rear view of an embodiment of a nose sensor.
Figure 8A:
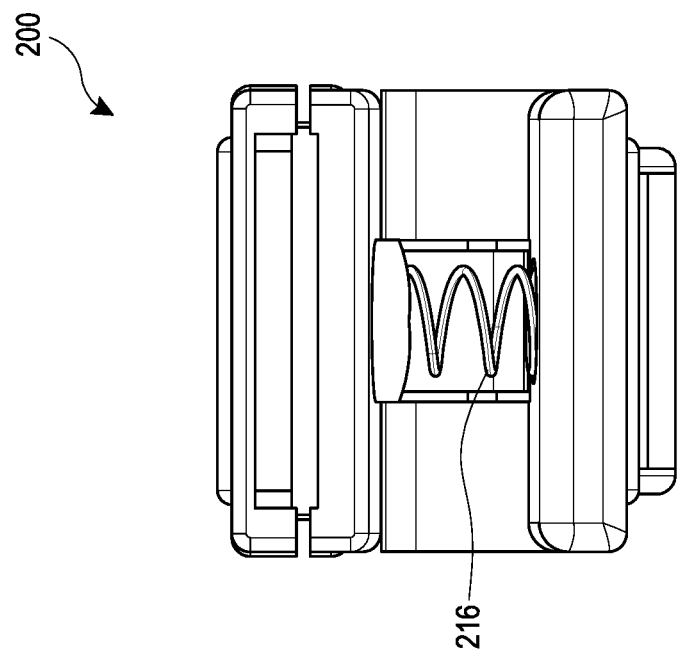
FIG. 8A illustrates a rear view of an embodiment of a nose sensor.

FIGS. 8A and 8B illustrate rear views of an embodiment of the nose sensor 200. For example, FIG. 8A illustrates a rear view of the nose sensor in a neutral position, as described in more detail above. FIG. 8B illustrates a rear view of the nose sensor 200 in a tilted position, as described in more detail above. As shown in FIGS. 8A and 8B, the biasing member 216 can act to allow the upper sensor body 204 to tilt and/or rotate relative to the lower sensor body 202 and return to a neutral position when no external forces are applied.

Figure 9:
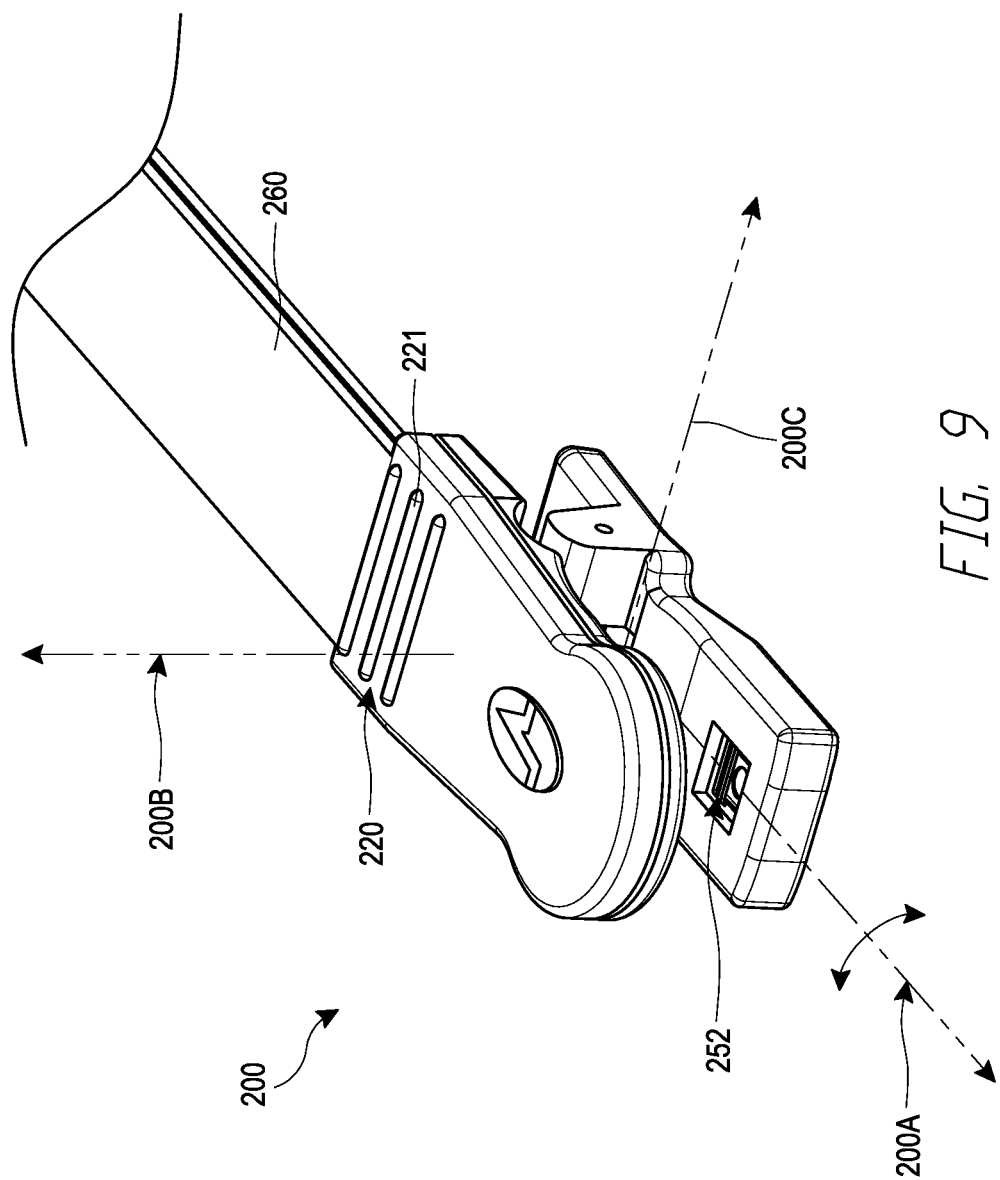
FIG. 9 illustrates a perspective view of an embodiment of a nose sensor.

FIG. 9 illustrates an example of the axes of rotation and/or tilt of the nose sensor 200. For example, the nose sensor 200 can include a longitudinal axis 200A and a transverse axis 200B. The longitudinal axis 200A can be approximately perpendicular to the transverse axis 200B. The upper sensor body 204 can be configured to rotate about the longitudinal axis 200A. However, rotation about the transverse axis 200B can be prevented. Such configurations can advantageously maintain an alignment between an emitter 254 and a detector 252 of the nose sensor, as described in more detail below. As also described herein, the upper sensor body 204 and/or the lower sensor body 202 can rotate about a rotational axis 200C, for example, when the biasing member 216 is compressed.

As shown in at least FIG. 9, for example, the nose sensor 200 can include a grip portion 220. The grip portion 220 can be positioned towards a rear of the nose sensor 200. For example, the grip portion 220 can include one or more ribs 221 to allow a user to easily grip the nose sensor 200 to open and/or close the nose sensor 200. The grip portion 220 can include three ribs 221. The one or more ribs 221 can be sized, shaped, and/or spaced to facilitate grip from a user, for example, for a user's fingers. The one or more ribs 221 can be evenly spaced. The one or more ribs 221 can be rounded. The one or more ribs 221 can alternatively not rounded. The grip portion 220 can include one, two, four, five, or six or more ribs 221. The grip portion 220 can be positioned on a rear portion of the upper sensor body 204 and/or the lower sensor body 202.

As shown in FIG. 9, the nose sensor 200 can have a cable 260. The nose sensor 200 can be configured to connect to a cable 260. The cable 260 can be configured to transmit signals sensed by the nose sensor 200 and/or certain physiological parameters measured by the nose sensor 200 to a patient monitoring system. The nose sensor 200 can wirelessly transmit data measured by and/or received by the sensor 200 to the patient monitoring device. The wireless transmission can be by a communication protocol such as those discussed above. The nose sensor 200 can include a wireless transmitter, a wireless receiver, and or a wireless transceiver for transmitting and/or receiving data and/or instructions.

As described herein, the nose sensor 200 can measure various physiological parameters of a patient, such as those discussed above. As shown in at least FIG. 9, for example, the nose sensor 200 can include an emitter 254 and a detector 252 to allow the nose sensor 200 to measure the patient's physiological parameters.

Various arrangements and/or configurations of the emitter 254 and the detector 252 can allow the nose sensor 200 to take more accurate measurements. For example, the emitter 254 can be a light-emitting diode (LED). The emitter 254 can emit light of a certain wavelength. The light emitter 254 can emit light of different wavelengths in sequence with only one emitter emitting light at a given time, thereby forming a pulse sequence. The number of emitters is not limiting and can range from two to eight. Detailed descriptions and additional examples of the light emitters are provided in U.S. Pat. No. 9,277,880, referenced above.

The detector 252 can detect light from the emitter 254 after the light passes through and is attenuated by tissue of the patient's nose. For example, the detector 252 can comprise photodetectors, photodiodes, phototransistors, and/or the like. Additional details of the photodetector are described in U.S. Pat. No. 9,277,880, referenced above. The detector 252 can generate an electrical signal based on the detected light from the emitter 254. The signal of the detected light from the emitter 254 can be input into a signal processor described herein, such that the signal processor can process an output of the sensor 200.

The nose sensor 200 can include a diffuser 258 which can allow the diffusion of light prior to entering the tissue. The diffuser 258 can advantageously spread out, disseminate, and/or scatter light exiting from the emitter 254 into and/or around a portion of a patient's body, for example. This can permit light originating from the emitter 254 to pass through a wider region or area of a patient's body, and thus better facilitate collection of physiological parameters (such as those discussed above). The detector 252 can be sized and shaped to receive the optical radiation after it attenuates through tissue and fluids of a portion of a body. Diffusing light prior to entering the tissue can be advantageous because the light is allowed to pass through more tissue. This allows the light to sample more of the body tissue before being detected. It also provides for more even and consistent light across a larger portion of tissue.

Figure 10B:
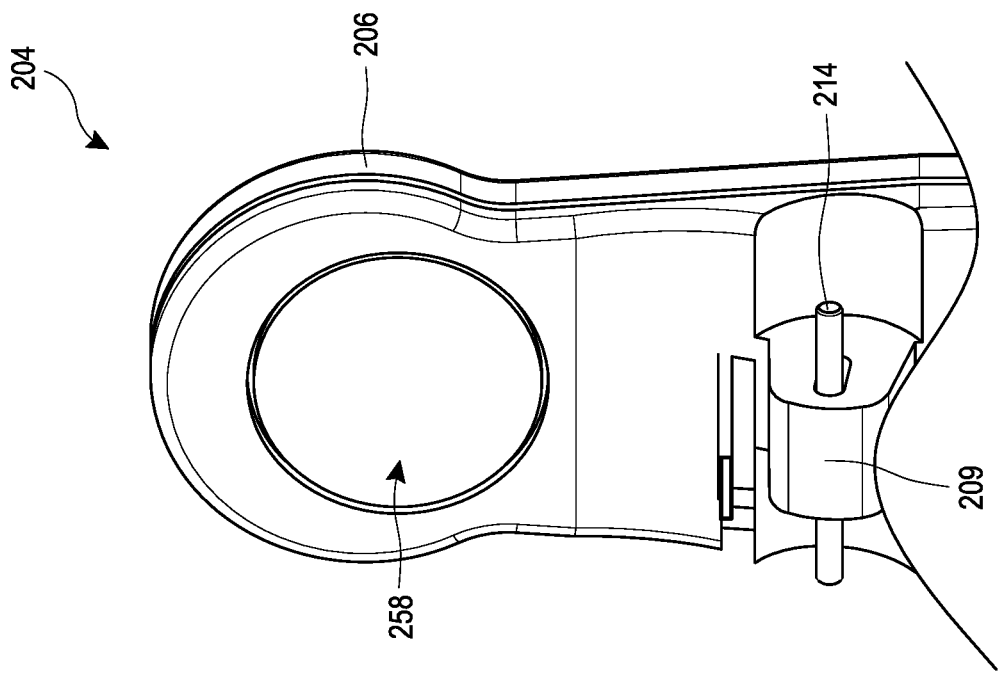
FIG. 10B illustrates a side perspective view of a portion of a sensor body of an embodiment of a nose sensor.
Figure 10A:
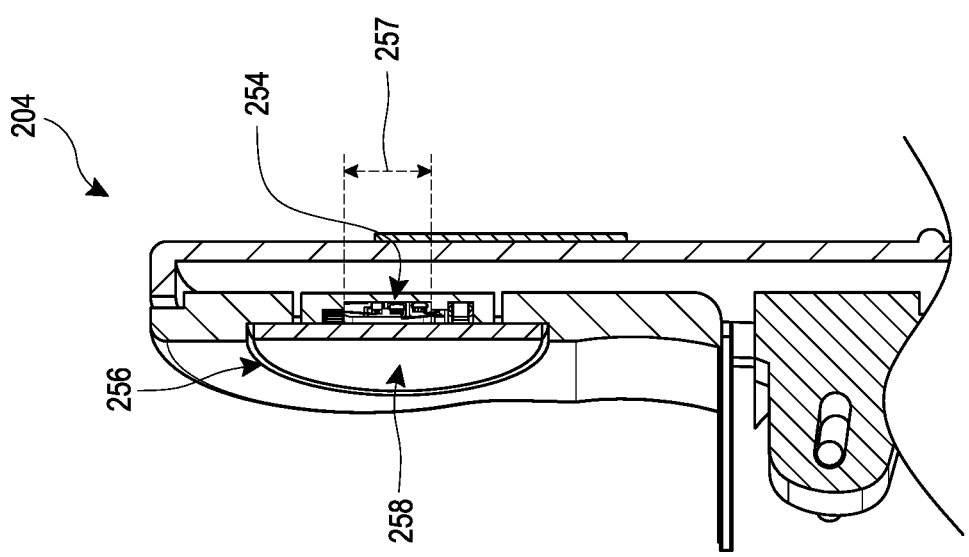
FIG. 10A illustrates a side cross-sectional view of a portion of an embodiment of a nose sensor.

FIGS. 10A and 10B illustrate an emitter 254 wherein a diffuser 258 is positioned proximate to the emitter 254 within the upper sensor body 204, for example, in front of the emitter 254. The emitter 254 can be positioned within the upper sensor body 204. The upper sensor body 204 can include a recess 256 shaped to fit the diffuser 258. When assembled, the diffuser 258 can be positioned within the recess 256 of the upper sensor body 204. Such configurations can advantageously assist in desensitizing the nose sensor 200 to various geometric variations. For example, positioning the diffuser 258 within a recess 256 of the upper sensor body 204 can reduce the bulkiness and/or the obtrusiveness of the nose sensor 200 while also including the diffuser 258 which affords benefits such as those discussed herein. Thus, the recess 256 in the upper sensor body 204 can allow the nose sensor 200 to maintain a low profile while still beneficially including a diffuser (see e.g., FIG. 10A).

The diffuser 258 can be entirely positioned within the recess 256 of the upper sensor body 204. The diffuser 258 can be at least partially positioned within the recess 256 of the upper sensor body 204. For example, a portion of the diffuser 258 can extend outside of the recess 256 of the upper sensor body 204.

The positioning of the diffuser 258 within the recess 256 of the upper sensor body 204 can allow for a diffuser 258 with increased thickness to be used. The positioning of the diffuser 258 within the recess 256 of the upper sensor body 204 can allow for a diffuser 258 to be used with an increased diameter. In certain configurations described herein, the diffuser 258 positioning, size, and/or thickness can advantageously provide greater homogeneity across the diffuser 258. The diffuser 258, when positioned in front of the emitter 254, can trade directionality and intensity (of light transmitted by the emitter 254) for homogeneity of illumination. The size and/or shape (e.g., thickness and/or diameter) of the diffuser 258 can help to avoid edge effects. Similarly, the proximity of the diffuser 258 relative to the emitter 254 can help to avoid edge effects. Such configurations can advantageously help to desensitize the nose sensor 200 to geometric variability. For example, the size and/or shape of the diffuser 258 and/or the positioning of the diffuser 258 can allow the nose sensor 200 to accommodate various nose shapes and/or sizes, and/or accurately measure a patient's physiological parameters.

The diffuser 258 can comprise silicone. For example, the diffuser 258 can include white silicone to scatter a greater amount of light and/or more accurately measure a patient's physiological parameters. The diffuser 258 can comprise materials other than silicone. For example, the diffuser 258 can comprise acrylic and/or plastics such as polycarbonate and/or polycarbonate film or sheets. The diffuser 258 can comprise glass such as opal glass, ground glass, patterned glass, and/or a combination of such materials. The diffuser 258 can also comprise other materials with varying material properties and/or characteristics. The diffuser 258 can comprise one or more layers with different material properties and/or characteristics. For example, the diffuser 258 can comprise, two or more, three or more, four or more, five or more, six or more, seven or more, or eight or more layers with different material properties and/or characteristics. Additionally, the diffuser 258 can comprise one or more layers with similar material properties and/or characteristics. For example, the diffuser 258 can comprise, two or more, three or more, four or more, five or more, six or more, seven or more, or eight or more layers with similar material properties and/or characteristics.

The nose sensor 200 can include a cover 206. The cover 206 can be coupled to an outer wall of the upper sensor body 204 to enclose the emitter 254. For example, the cover 206 can be coupled to the upper sensor body in a snap-fit configuration such that the cover 206 snaps into place to enclose the emitter 254. The cover 206 can advantageously retain the emitter 254 in the proper position. The cover 206 can advantageously isolate the area in front of the emitter 254 so as to prevent external light from entering the portion of the patient's nose where the emitter 254 is configured to emit light into. This can reduce inaccuracies and/or imprecision involved in the measuring of physiological parameters by the nose sensor 200.

As shown in at least FIGS. 2A and 9, the nose sensor 200 can include a detector 252. The detector 252 can be positioned within the lower sensor body 202. For example, the lower sensor body 202 can include an opening formed in an inner surface of the lower sensor body 202 to allow the detector 252 to more easily detect light. The nose sensor 200 can include a shield and/or screen over the opening which can cover the detector 252. The nose sensor 200 can include a lens on and/or around the detector 252. This lens can advantageously help focus light into the detector 252. For example, the lens can help focus light transmitted through a portion of a patient's body, such as a nose, and originating from the emitter 254. The lens can comprise various materials. For example, the lens can comprise glass and/or plastic. The lens can also comprise various optical refractive properties. For example, the lens can vary in thickness, curvature, refractive index, focal length, and/or other properties. The lens can be a simple lens. For example, the lens can comprise a single piece of transparent material. Alternatively, the lens can be a compound lens. For example, the lens can comprise one or more simple lenses arranged about a common axis. For example, the lens can comprise two or more, three or more, four or more, five or more, or six or more simple lenses arranged about a common axis.

In the neutral position, the emitter 254 can be positioned approximately parallel to the detector 252. In use, the detector 252 can be positioned within the lower sensor body 202 such that the emitter 254 remains in alignment with the detector 252 as the nose sensor 200 is attached to a patient. Thus, the emitter 254 can remain in alignment with the detector 252 regardless of the shape and/or size of the patient's nose. This can advantageously allow for accurate measurements of physiological parameters to be collected.

As shown in FIG. 10A, the diffuser 258 can remain aligned with at least a portion of the emitter 254 in use. For example, an emitter active area 257 can be positioned along at least a portion of the diffuser 258. Such configurations can allow the diffuser 258 and emitter 254 to remain aligned, and can also allow light emitted from the emitter 254 to be appropriately aimed at the diffuser 258. Such configurations can allow for greater homogeneity across the diffuser 258, as diffusers 258 with increased diameters and/or thicknesses can be used as discussed herein.

In use, when the nose sensor 200 is attached to the patient, for example, clipped onto the patient, the detector 252 can be configured to be positioned within the patient's nose, while the emitter 254 can be configured to remain outside of the patient's nose in alignment with the detector 252. Alternatively, when the nose sensor 200 is attached to the patient, for example, clipped onto the patient, the emitter 254 can be configured to be positioned within the patient's nose, while the detector 252 can be configured to remain outside of the patient's nose in alignment with the emitter 254. Thus, the nose sensor 200 can accurately measure a patient's physiological parameters when the nose sensor 200 is attached to the patient.

Figure 11:
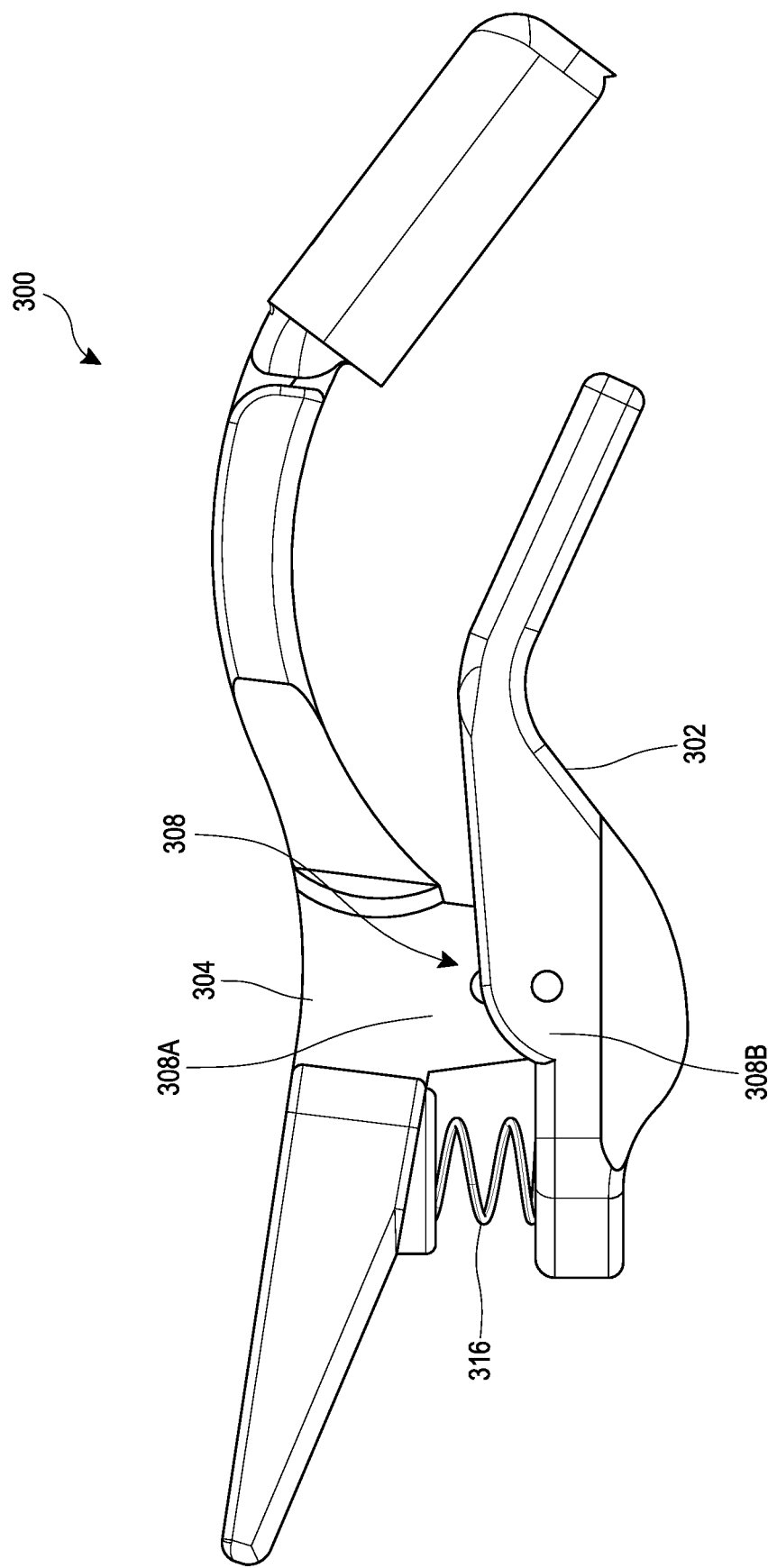
FIG. 11 illustrates an embodiment of a nose sensor.

FIG. 11 illustrates an alternative design of the nose sensor 300. The nose sensor 300 can be similar to or identical to the nose sensor 200 discussed above in any or all respects. As shown in FIG. 11, the nose sensor 300 can include an upper sensor body 304, a lower sensor body 302, and a joint 308, which can be respectively similar to the upper sensor body 204, the lower sensor body 202, and the joint 208 as described above in connection with the nose sensor 200. The nose sensor 300 can include any one, or any combination, of features of the nose sensor 200. For example, the nose sensor 300 can include the diffuser 258 and/or the lens discussed above.

For example, the nose sensor 300 can include a lower sensor body 302. The lower sensor body 302 may be the same or otherwise substantially similar to the lower sensor body 202 discussed above in connection with the nose sensor 200.

Figure 12C:
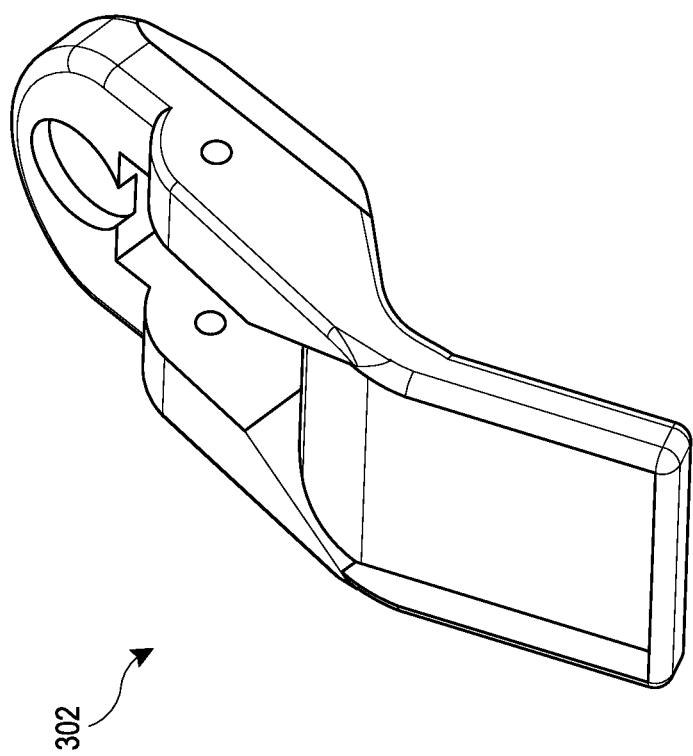
FIG. 12C illustrates a perspective view of a lower sensor body of an embodiment of a nose sensor.
Figure 12E:
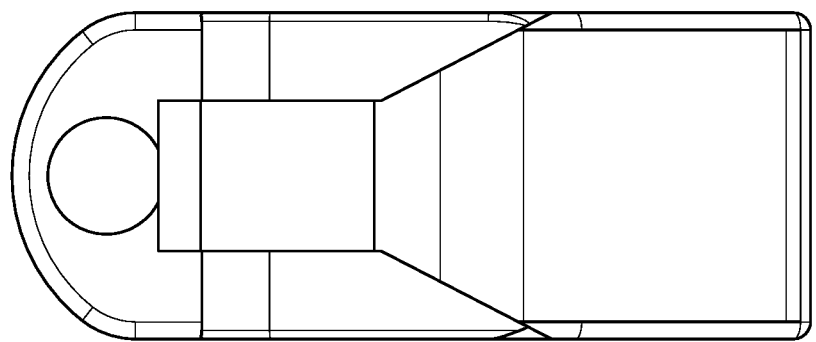
FIG. 12E illustrates a top view of a lower sensor body of an embodiment of a nose sensor.
Figure 12D:
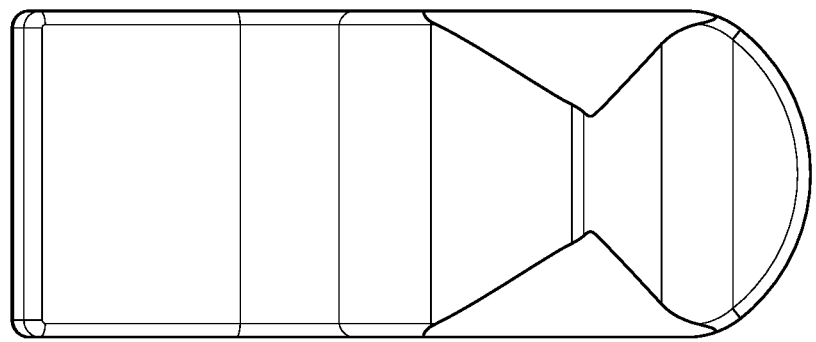
FIG. 12D illustrates a bottom view of a lower sensor body of an embodiment of a nose sensor.

As shown in FIGS. 11-12E, the lower sensor body 302 can be generally curved. For example, the lower sensor body 302 can include a rear portion, an intermediate portion, and a front portion. The rear portion and the front portion of the lower sensor body 302 are connected by the intermediate portion. Generally, the rear portion, the intermediate portion, and the front portion of the lower sensor body 302 are integrally formed. As shown, the rear portion smoothly transitions to the front portion along the intermediate portion.

For example, as shown in FIGS. 12A-12E, the rear portion can be generally flat. The biasing member, as discussed in more detail below, can be attached to a flat portion of the rear portion of the lower sensor body 302. The rear portion can be angled upwards towards the joint 308.

Generally, the intermediate portion of the lower sensor body 302 can be curved and/or inclined. For example, the intermediate portion can be inclined from the joint towards the front portion. The intermediate portion of the lower sensor body 302 can be formed with the rear portion by a step. The step can be rounded, flat, curved, and/or squared. For example, the intermediate portion can be positioned at least partially above the rear portion when the lower sensor body 302 is positioned in the neutral position (for example, when no and/or minimal external forces are applied to the nose sensor).

The front portion of the lower sensor body 302 can be generally tapered and/or angled. For example, as shown, the front portion extends at an angle downwards relative to the intermediate portion away from the rear portion of the lower sensor body 302. Such configurations can advantageously allow at least the intermediate and/or front portion of the lower sensor body 302 to conform to an inner wall of the patient's nose. Thus, the lower sensor body 302 can more easily accommodate various nose shapes and sizes. This can enhance the overall comfort to the patient of wearing the nose sensor 300.

The nose sensor 300 can include an upper sensor body 304. The upper sensor body 304 may be the same or otherwise substantially similar to the upper sensor body 204 discussed above in connection with the nose sensor 200.

Figure 13D:
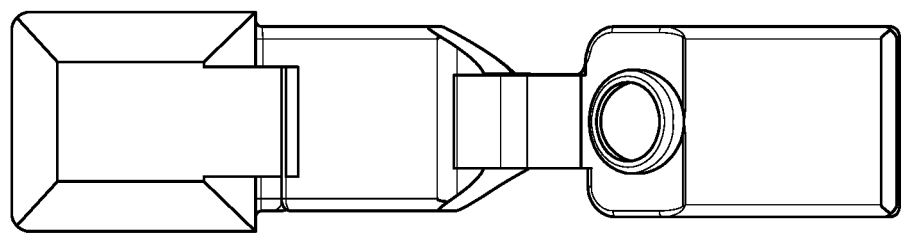
FIG. 13D illustrates a bottom view of an upper sensor body of an embodiment of a nose sensor.
Figure 13C:
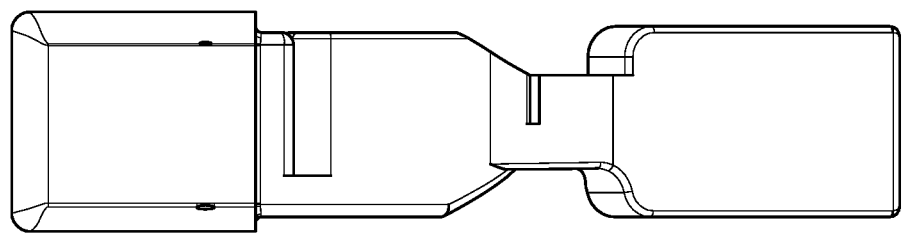
FIG. 13C illustrates a top view of an upper sensor body of an embodiment of a nose sensor.

As shown in at least FIGS. 11 and 13A-13B, the upper sensor body 304 can be generally curved. For example, the upper sensor body can include a rear portion, an intermediate portion, and a front portion. The rear portion and the front portion of the upper sensor body 304 are connected by the intermediate portion. Generally, the rear portion, intermediate portion, and the front portion of the upper sensor body 304 are integrally formed. As shown, the rear portion smoothly transitions to the front portion along the intermediate portion.

Generally, the intermediate portion of the upper sensor body 304 can be curved and/or inclined. For example, as shown in FIGS. 13A-13D, the intermediate portion can include a convex portion and a concave portion. As shown, as the upper sensor body 304 extends along a length of the nose sensor 300, the upper sensor body 304 can be angled downwards towards from the rear portion towards the joint 308 along the convex portion and/or upwards towards the front portion from the joint 308 along the concave portion. As a result, an apex of the convex portion of the intermediate portion can be positioned lower than an apex of the concave portion of the intermediate portion. Such configurations can advantageously follow or conform to a shape of a patient's nostril and/or curved nose shape.

The front portion of the upper sensor body 304 can be angled downwards away from the rear portion. The front portion of the upper sensor body 304 can include the same and/or similar curvature and/or shape as the front portion of the lower sensor body 302 to allow the upper sensor body 304 and the lower sensor body 302 to remain spaced apart by a same distance along the length of the nose sensor 300 when the nose sensor is in the neutral position (for example, no and/or minimal external forces are applied to the nose sensor).

Such configurations of the nose sensor 300 described herein can advantageously conform to the inner and/or outer walls of the patient's nose and/or can accommodate various nose shapes and/or sizes. For example, in use, at least the front portion of the lower sensor body 302 can be configured to be inserted into and conform to a patient's nose and engage an inner side wall of the patient's nose. In such configurations, at least the concave portion of the intermediate portion and the front portion of the upper sensor body 304 can be configured to be secured to an outer wall of the patient's nose (for example, the alar region of the patient's nose). The general curvature and/or shape of the upper sensor body 304 and/or the lower sensor body 302 can allow the nose sensor 300 to easily accommodate various nose shapes and sizes. For example, the shape of the intermediate region and/or the front region of the lower sensor body 302 can conform to an inner surface of the patient's nose. In some examples, the shape of the intermediate region and/or the front region of the upper sensor body 304 can conform to an outer surface of the patient's nose. Such configurations allow the nose sensor 300 to maintain a low profile and/or thickness. The upper sensor body 304 and/or the lower sensor body 302 can have a reduced width. The reduced thickness and/or width of the nose sensor 300 can reduce the overall bulkiness of the sensor. Accordingly, the nose sensor 300 can be relatively lightweight and take up less space when secured to the patient, inside and/or outside of the patient's nose. Thus, the nose sensor 300 can be less obtrusive and/or have enhanced aesthetics.

The upper sensor body 302 can have a greater length relative to the lower sensor body 304. For example, the front portion of the upper sensor body can be positioned at least partially or in some instances entirely forwards of the lower sensor body 302. Such configurations can advantageously help to reduce stress and strain on the joint 308 and/or provide better coupling to the communications link.

The upper sensor body 304 can be spaced apart from the lower sensor body 302 by a biasing member 316 (see FIG. 11). The biasing member 316 can be similar to or identical to the biasing member 216 discussed above in any or all respects. For example, the biasing member 316 can include a compression spring, among other materials described herein. Where the biasing member 316 includes a compression spring, the spring can comprise various strength and/or stiffness properties, and/or other material properties. The biasing member 316 can be in contact with or be coupled to the upper sensor body 304 and/or the lower sensor body 302. For example, the upper sensor body 304 can include a protrusion and/or recess for receiving one end of the biasing member 316. The protrusion and/or recess can have an increased height or depth to reduce the likelihood that the biasing member 316 would fall out and/or be disengaged from a portion of the nose sensor 300. The biasing member 316 can be adhered to the inner surface of the upper sensor body 304 and/or the lower sensor body 302.

The nose sensor 300 can include a joint 308, which can be similar or identical to the joint 208, in any or all respects. The joint 308 can include an upper joint 308A and a lower joint 308B (see FIG. 11). As shown, the lower joint 308B may be formed in the lower sensor body 302. For example, the lower joint 308B can be formed in the intermediate portion of the lower sensor body 302. The lower joint 308B can be formed in the step of the intermediate portion of the lower sensor body 302. Such configurations can provide a nose sensor 300 having a reduced profile, as the upper sensor body 304 may be positioned closer to the lower sensor body 302.

The nose sensor 300 discussed herein can measure various physiological parameters of a patient, such as those discussed above. The nose sensor 300 can include an emitter 354 and a detector 352 to allow the nose sensor 300 to measure the patient's physiological parameters. The emitter 354 and/or the detector 353 can be similar to or identical to the emitter 254 and/or the detector 252 of the nose sensor 200, in any or all respects.

The emitter 354 can be coupled to the upper sensor body 304 and the detector 352 can be coupled to the lower sensor body 302. However, the emitter 354 can be coupled to the lower sensor body 302 and the detector 352 can be coupled to the upper sensor body 304.

FIG. 11 shows an alternative design of the nose sensor 300 which can include an emitter 354 (not shown) coupled to the upper sensor body 304. The emitter 354 can be positioned within an aperture in the upper sensor body 304. The emitter 354 can be coupled directly with an inner surface 350 of a front portion of the upper sensor body 304 (see FIG. 13A). For example, the emitter 352 may not be positioned within an aperture in the upper sensor body 304. The upper sensor body 304 can be coupled to, or is integrally formed with, a spacer 370 (see FIG. 14). Spacer 370 can comprise various shapes and/or sizes, so as to fit within at least a portion of the upper sensor body 304, such as the inner surface 350. For example, the spacer 370 can comprise a pyramid-like shape (see FIG. 14). The spacer 370 can comprise a pyramid-like shape and also includes an opening in a center portion which allows at least a portion of the emitter 354 to be placed therewithin. The spacer 370 can space the emitter 354 outwardly from an inner surface 350 of the upper sensor body 304 (see FIG. 13A). Such configurations can advantageously allow the emitter 354 to be positioned closer to the skin of the patient, which can help to maintain engagement between the emitter 354 and the patient. For example, the spacer 370 can be positioned between the inner surface 350 of the upper sensor body 304 and the emitter 354. The nose sensor 300 can include a diffuser at or around the emitter 354 and/or at the opening in the spacer 370. This diffuser can be similar or identical to the diffuser discussed above with reference to nose sensor 200 and emitter 254 in any or all respects.

Figure 14:
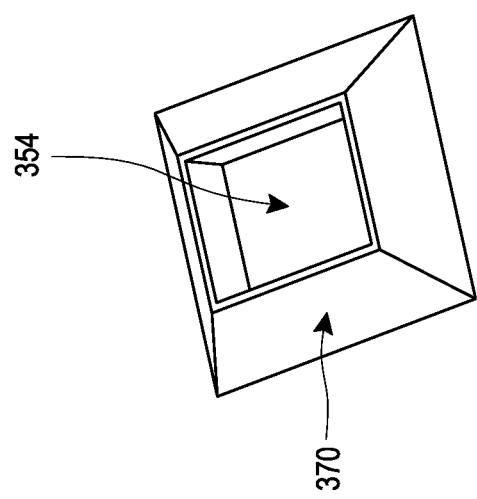
FIG. 14 illustrates a spacer of an embodiment of a nose sensor.
Figure 14:
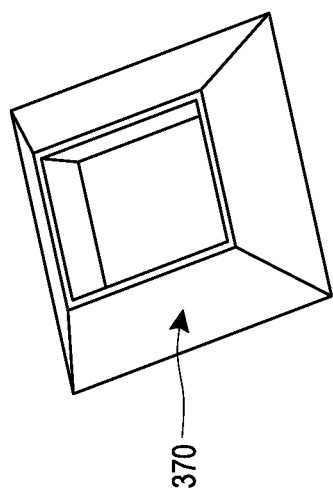

As shown in FIG. 14, for example, the emitter 354 can be encased and/or enclosed by the spacer 370. The spacer 370 can encase at least a portion of the emitter 354. For example, the spacer 370 can encase the emitter 354 leaving an inner face open (for example, a face of the emitter 354 that faces the detector 352 in use). For example, the spacer 370 can include an opening in which the emitter 354 is positioned. The spacer 370 can increase the amount of light that enters the patient's nose, similar to the diffuser discussed above. For example, the spacer 370 can include a material that surrounds the emitter 352 and/or the opening in the spacer 370 to spread or scatter light before entering the patient's skin. The material can include white dynaflex, and/or ceramic, among other materials, and/or coatings, such as a clear versaflex.

Figure 15:
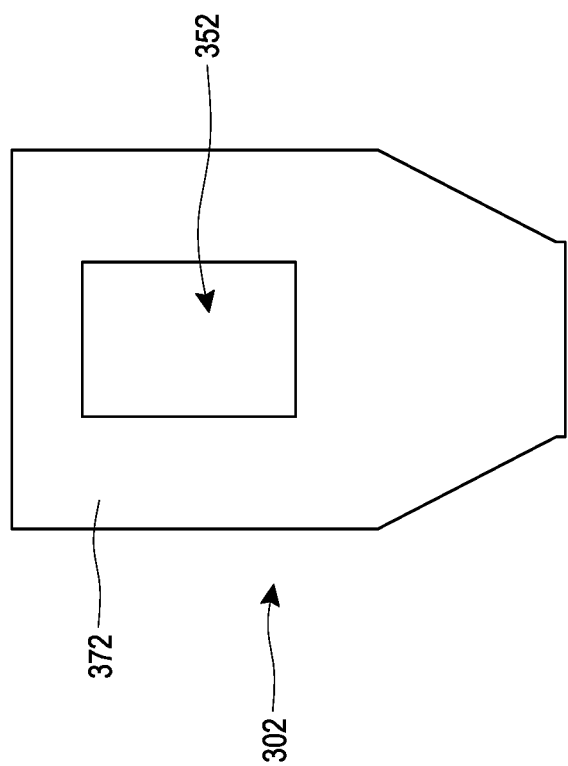
FIG. 15 illustrates a portion of a lower sensor body of an embodiment of a nose sensor.

The detector 352 can be coupled to the lower sensor body 302. For example, the detector 352 can be adhered to an inner surface of the front portion of the lower sensor body 302. As shown in FIG. 15, the lower sensor body 302 can include the detector 352. The nose sensor 300 can include a lower sensor body cover 372 which can be coupled to an outer wall of the lower sensor body 302 to enclose the detector 352. For example, the cover 372 can be coupled to the lower sensor body 302 in a snap-fit configuration such that the cover 372 snaps into place to enclose the detector 352. The cover 372 can be configured to prevent external and/or stray light from reaching the detector 352. For example, when the nose sensor 300 is secured to a portion of a patient's body, such as a nose, the cover 372 can surround and enclose the detector 352 so that external light is not allowed to contact the detector 352. This can ensure that the detector 352 receives primarily (or only) light and/or optical radiation that originates from the emitter 354 and attenuates through the patient's tissue and/or fluids, as opposed to external or stray light. This configuration can advantageously increase the accuracy of the physiological measurements collected from the nose sensor 300. The cover 372 can comprise silicone, such as a black silicone and/or other materials. The cover 372 can advantageously provide a biocompatible barrier over the detector 352. The black silicone of the cover 372 can help to prevent stray light from reaching the detector 352 as described above. The cover 372 can include a rim extending along a perimeter of the cover 372 which, when adjacent to a patient's skin during nose sensor 300 securement to a nose, additionally helps prevent external light from getting to the detector 352. Such configurations can advantageously provide more accurate measurements.

The nose sensor 300 can include a lens on and/or around the detector 352. This lens can advantageously help focus light into the detector 352. For example, the lens can help focus light transmitted through a portion of a patient's body, such as a nose, and originating from the emitter 354. The lens can comprise various materials. For example, the lens can comprise glass and/or plastic. The lens can also comprise various optical refractive properties. For example, the lens can vary in thickness, curvature, refractive index, focal length, and/or other properties. The lens can be a simple lens. For example, the lens can comprise a single piece of transparent material. Alternatively, the lens can be a compound lens. For example, the lens can comprise one or more simple lenses arranged about a common axis. For example, the lens can comprise two or more, three or more, four or more, five or more, or six or more simple lenses arranged about a common axis.

As discussed above, the emitter 354 can be coupled to the upper sensor body 304 and the detector 352 can be coupled to the lower sensor body 302. The upper sensor body 304 is configured to conform to an outer surface of the patient's nose, while the lower sensor body 302 is configured to be inserted into a patient's nose and conform to an inner wall of the patient's nose. In use, the emitter 354 (for example, which is positioned outside of the nose) is configured to be directed towards the detector 352 (for example, which is positioned inside of the nose). Such configurations can provide more comfort to the patient. Such configurations can provide higher PI values, more stable ratios and/or measurements, and/or more accurate measurements of the patient's physiological parameters, among others.

Figure 16:
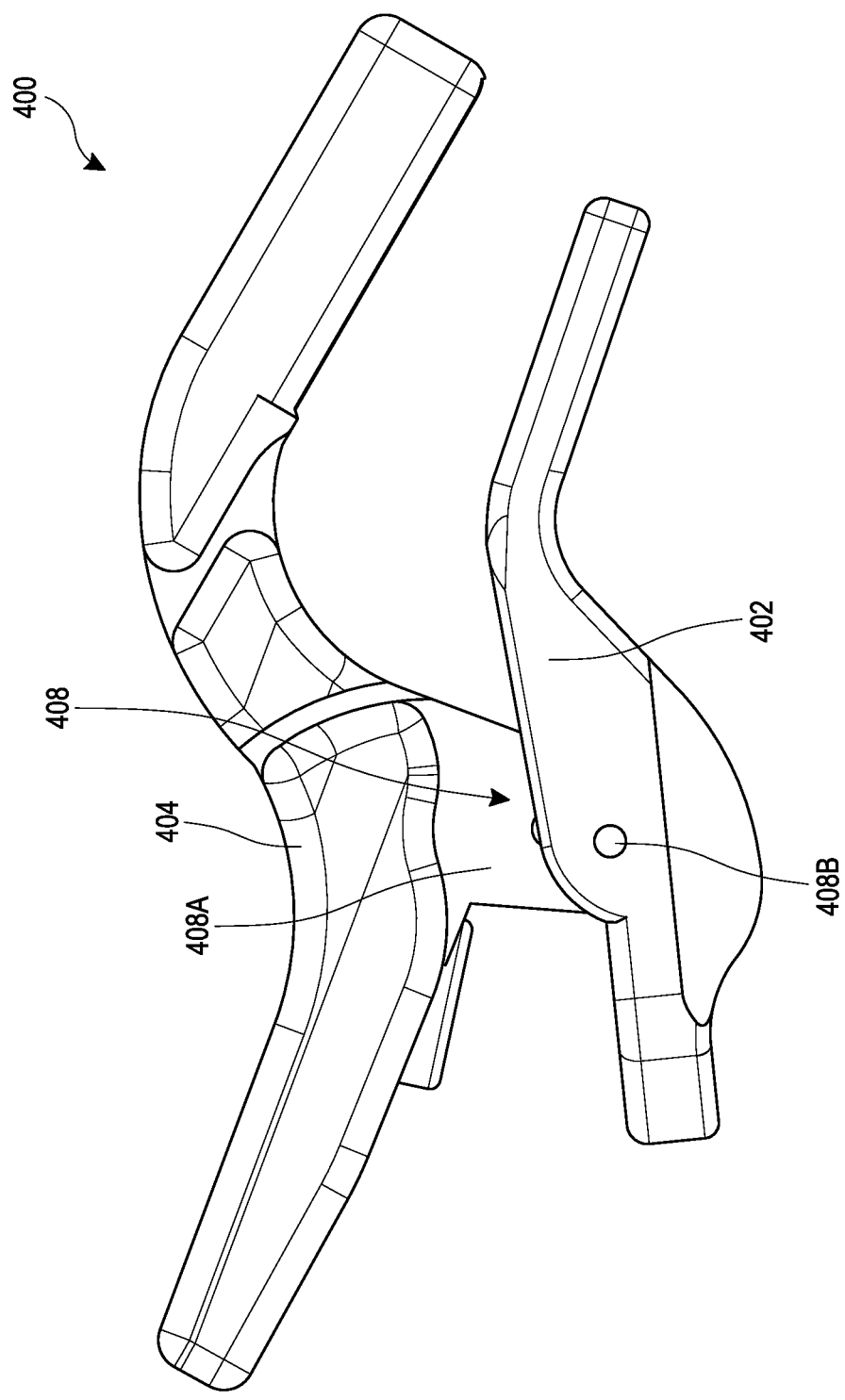
FIG. 16 illustrates an embodiment of a nose sensor.

FIG. 16 illustrates an alternative design of the nose sensor 400. The nose sensor 400 can be similar to or identical to the nose sensors discussed above in any or all respects. As shown in FIG. 16, the nose sensor 400 can include an upper sensor body 404, a lower sensor body 402, and a joint 408, which can be respectively similar to the upper sensor body 204, 304, the lower sensor body 202, 302, and the joint 208, 308 described above in connection with the nose sensors 200, 300. The nose sensor 400 can include any one, or any combination, of features of the nose sensors 200, 300. For example, the nose sensor 400 can include a lens, diffuser, cover, spacer, joint, and/or other features described with reference to nose sensors 200, 300.

Although this disclosure has been disclosed in the context of certain preferred embodiments and examples, it will be understood by those skilled in the art that the present disclosure extends beyond the specifically disclosed embodiments to other alternative embodiments and/or uses of the disclosure and obvious modifications and equivalents thereof. In addition, while a number of variations of the disclosure have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. Accordingly, it should be understood that various features and aspects of the disclosed embodiments can be combined with or substituted for one another in order to form varying modes of the disclosed.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. Additionally, as used herein, "gradually" has its ordinary meaning (e.g., differs from a non-continuous, such as a step-like, change).

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A noninvasive physiological monitoring device configured to be secured to a nose of a patient, the device comprising:
    an upper sensor body comprising a front portion, a rear portion, and an intermediate portion positioned between the front and rear portions, wherein the intermediate portion of the upper sensor body is curved;
    a lower sensor body comprising a front portion, a rear portion, and an intermediate portion positioned between the front and rear portions;
    an emitter configured to emit light of one or more wavelengths towards tissue of the nose of the patient, wherein the emitter is positioned at the front portion of the upper sensor body;
    a detector configured to detect at least a portion of the light emitted from the emitter after attenuation through the tissue of the nose of the patient, wherein the detector is positioned at the front portion of the lower sensor body and is further configured to the generate one or more signals responsive to the detected at least the portion of the light; and
    a joint configured to rotatably couple the upper sensor body to the lower sensor body, the joint including:
        an upper joint comprising a slot, wherein the upper joint extends from the upper sensor body towards the lower sensor body;
        a first lower joint comprising a first hole, wherein the first lower joint is proximate a first side of the lower sensor body, and wherein the first lower joint extends from the lower sensor body towards the upper sensor body;
        a second lower joint comprising a second hole, wherein the second lower joint is proximate a second side of the lower sensor body, and wherein the second lower joint extends from the lower sensor body towards the upper sensor body; and
        a pin configured to extend through at least a portion of the slot of the upper joint and the first hole of the first lower joint and the second hole of the second lower joint;
    wherein the upper joint is positioned between the first lower joint and the second lower joint and the slot of the upper joint allows the upper sensor body to at least partially rotate about a longitudinal axis of the device, the longitudinal axis extending along a length of the device;
    wherein the joint prevents the upper sensor body from rotating about a transverse axis of the device, the transverse axis extending along a height of the device, the transverse axis being perpendicular to the longitudinal axis;
    wherein the joint is further configured to allow the upper and lower sensor bodies to rotate with respect to each other between a first position and a second position, the first position being a neutral position, the front portions of the upper and lower sensor bodies closer to each other when in the neutral position than when in the second position;
    wherein, when the upper and lower sensor bodies are in the neutral position, the front portion of the upper sensor body is angled with respect to the front portion of the lower sensor body, and wherein, when the upper and lower sensor bodies are in the second position, the front portion of the upper sensor body is parallel with respect to the front portion of the lower sensor body.

2. The noninvasive physiological monitoring device of claim 1, further comprising a biasing member coupled to the rear portion of the upper sensor body and the rear portion of the lower sensor body.

3. The noninvasive physiological monitoring device of claim 2, wherein a greater force is applied to the biasing member when the upper and lower sensor bodies are in the second position than when in the neutral position.

4. The noninvasive physiological monitoring device of claim 1, wherein the intermediate portion of the upper sensor body comprises a convex portion and a concave portion.

5. The noninvasive physiological monitoring device of claim 1, wherein the slot of the upper joint allows the upper and lower sensor bodies to move vertically with respect to one another.

6. The noninvasive physiological monitoring device of claim 1, further comprising a signal processor in communication with the detector, the signal processor configured to generate a measurement of one or more physiological parameters based on the generated one or more signals.

7. The noninvasive physiological monitoring device of claim 1, further comprising a lens configured to focus at least a portion of the attenuated light into the detector.

8. The noninvasive physiological monitoring device of claim 1, wherein the upper sensor body comprises a first length and the lower sensor body comprises a second length, and wherein the first length is greater than the second length.

9. The noninvasive physiological monitoring device of claim 1, wherein the upper joint extends from the intermediate portion of the upper sensor body and wherein the first and second lower joints extend from the intermediate portion of the lower sensor body.

10. The noninvasive physiological monitoring device of claim 1, wherein the intermediate portion of the upper sensor body is curved in a first direction and a second direction opposite the first direction.

11. The noninvasive physiological monitoring device of claim 1, further comprising a diffuser positioned within a recess of the upper sensor body and configured to diffuse the emitted light into the tissue of the nose of the patient.

12. A method of calculating a measurement of one or more physiological parameters of a patient, comprising:
    transmitting light, with an emitter of a nose sensor, of at least first and second wavelengths through tissue of a nose of the patient;
    detecting, with a detector of the nose sensor, light attenuated by the tissue of the nose of the patient and generating one or more output signals based on the detected light; and determining the measurement of the one or more physiological parameters, with the nose sensor, based on the generated one or more output signals;

wherein the nose sensor includes:
an upper sensor body comprising a front portion, a rear portion, and an intermediate portion positioned between the front and rear portions, the emitter being positioned in the front portion of the upper sensor body, wherein the intermediate portion of the upper sensor body is curved;
a lower sensor body comprising a front portion, a rear portion, and an intermediate portion positioned between the front and rear portions, the detector being positioned in the front portion of the lower sensor body;
a joint configured to rotatably couple the upper sensor body to the lower sensor body, the joint including:
an upper joint comprising a slot, wherein the upper joint extends from the upper sensor body towards the lower sensor body;
a first lower joint comprising a first hole, wherein the first lower joint is proximate a first side of the lower sensor body, and wherein the first lower joint extends from the lower sensor body towards the upper sensor body;
a second lower joint comprising a second hole, wherein the second lower joint is proximate a second side of the lower sensor body, and wherein the second lower joint extends from the lower sensor body towards the upper sensor body; and
a pin configured to extend through at least a portion of the slot of the upper joint and the first hole of the first lower joint and the second hole of the second lower joint;
wherein the slot of the upper joint allows the upper sensor body to at least partially rotate about a longitudinal axis of the device, the longitudinal axis extending along a length of the device, and wherein the joint prevents the upper sensor body from rotating about a transverse axis of the device, the transverse axis extending along a height of the device the transverse axis being perpendicular to the longitudinal axis,
wherein the joint is further configured to allow the upper and lower sensor bodies to rotate with respect to each other between a first position and a second position, the first position being a neutral position, the front portions of the upper and lower sensor bodies closer to each other when in the neutral position than when in the second position, and
wherein, when the upper and lower sensor bodies are in the neutral position, the front portion of the upper sensor body is angled with respect to the front portion of the lower sensor body, and wherein, when the upper and lower sensor bodies are in the second position, the front portion of the upper sensor body is parallel with respect to the front portion of the lower sensor body.

13. The method of claim 12, wherein the method further comprises:
focusing light attenuated by the tissue of the nose of the patient into the detector with a lens.

14. The method of claim 12, wherein the nose sensor further comprises a diffuser positioned within a recess of the upper sensor body and wherein the method further comprises diffusing the emitted light into the tissue of the nose of the patient.

15. The method of claim 12, wherein the method further comprises moving the upper joint vertically with respect to the lower joint and allowing the upper sensor body to at least partially rotate about the longitudinal axis of the device.

16. A noninvasive physiological monitoring device configured to be secured to a nose of a patient, the device comprising:
an upper sensor body comprising a front portion, a rear portion, and an intermediate portion positioned between the front and rear portions;
a lower sensor body comprising a front portion, a rear portion, and an intermediate portion positioned between the front and rear portions;
an emitter configured to emit light of one or more wavelengths towards tissue of the nose of the patient, wherein the emitter is positioned at the front portion of the upper sensor body;
a detector configured to detect at least a portion of the light emitted from the emitter after attenuation through the tissue, wherein the detector is positioned at the front portion of the lower sensor body and is configured to generate one or more signals responsive to the detected at least the portion of the light; and
a joint configured to allow the upper and lower sensor bodies to rotate with respect to each other between a first position and a second position, the first position being a neutral position, the front portions of the upper and lower sensor bodies closer to each other when in the neutral position than when in the second position;
wherein, when the upper and lower sensor bodies are in the neutral position, the front portion of the upper sensor body is angled with respect to the front portion of the lower sensor body, and wherein, when the upper and lower sensor bodies are in the second position, the front portion of the upper sensor body is parallel with respect to the front portion of the lower sensor body;
wherein the joint comprises:
an upper joint comprising a slot, wherein the upper joint extends from the upper sensor body towards the lower sensor body;
a first lower joint comprising a first hole, wherein the first lower joint is proximate a first side of the lower sensor body, and wherein the first lower joint extends from the lower sensor body towards the upper sensor body;
a second lower joint comprising a second hole, wherein the second lower joint is proximate a second side of the lower sensor body, and wherein the second lower joint extends from the lower sensor body towards the upper sensor body; and
a pin configured to extend through at least a portion of the slot of the upper joint and the first hole of the first lower joint and the second hole of the second lower joint,
wherein the upper joint is positioned between the first lower joint and the second lower joint and the slot of the upper joint allows the upper sensor body to at least partially rotate about a longitudinal axis of the device, the longitudinal axis extending along a length of the device,
wherein the joint prevents the upper sensor body from rotating about a transverse axis of the device, the transverse axis extending along a height of the device and perpendicular to the longitudinal axis.

17. The noninvasive physiological monitoring device of claim 16, further comprising a biasing member coupled to the rear portion of the upper sensor body and the rear portion of the lower sensor body, wherein a greater force is applied to the biasing member when the upper and lower sensor bodies are in the second position than when in the neutral position.

\* \* \* \* \*